United States Patent
Jurak et al.

(10) Patent No.: US 9,949,655 B2
(45) Date of Patent: Apr. 24, 2018

(54) METHOD OF EKG SIGNAL PROCESSING AND APPARATUS FOR PERFORMING THE METHOD

(71) Applicants: USTAV PRISTROJOVE TECHNIKY AV CR, v.i.i., Brno (CZ); FAKULTNI NEMOCNICE U SV. ANNY V BRNE, Brno (CZ); M & I, SPOL. S.R.O., Prague (CZ)

(72) Inventors: Pavel Jurak, Brno (CZ); Josef Halamek, Brno (CZ); Vlastimil Vondra, Brno (CZ); Ivo Viscor, Brno (CZ); Petr Klimes, Brno (CZ); Filip Plesinger, Brno (CZ); Pavel Leinveber, Policka (CZ); Petr Vesely, Tisnov (CZ); Tereza Reichlova, Brno (CZ); Josef Sumbera, Brno (CZ); Jaroslav Meluzin, Bilovice Nad Svitavou (CZ); Karel Zeman, Slapanice (CZ); Miroslav Novak, Brno (CZ); Jolana Lipoldova, Brno (CZ); Michal Kuna, Prague (CZ)

(73) Assignees: USTAV PRISTROJOVE TECHNIKY AV CR, v.i.i., Brno (CZ); FAKULTNI NEMOCNICE U SV. ANNY V BRNE, Brno (CZ); M & I, SPOL. S.R.O., Praha (CZ)

( * ) Notice: Subject to any disclaimer, the term of this patent is extended or adjusted under 35 U.S.C. 154(b) by 52 days.

(21) Appl. No.: 15/105,926

(22) PCT Filed: Dec. 19, 2014

(86) PCT No.: PCT/CZ2014/000163
§ 371 (c)(1),
(2) Date: Jun. 17, 2016

(87) PCT Pub. No.: WO2015/090260
PCT Pub. Date: Jun. 25, 2015

(65) Prior Publication Data
US 2017/0007140 A1 Jan. 12, 2017

(30) Foreign Application Priority Data
Dec. 20, 2013 (CZ) .................................. 2013-1052

(51) Int. Cl.
*A61B 5/00* (2006.01)
*A61B 5/04* (2006.01)
(Continued)

(52) U.S. Cl.
CPC ...... *A61B 5/04014* (2013.01); *A61B 5/02028* (2013.01); *A61B 5/044* (2013.01);
(Continued)

(58) Field of Classification Search
CPC ... A61B 5/0452–5/0472; A61B 5/7253; A61B 5/7235; A61B 5/7264
See application file for complete search history.

(56) References Cited

U.S. PATENT DOCUMENTS

| 4,792,145 A | 12/1988 | Eisenberg et al. |
| 5,655,540 A | 8/1997 | Seegobin |

FOREIGN PATENT DOCUMENTS

| WO | 02075584 A1 | 9/2002 |
| WO | 03005900 A1 | 1/2003 |

(Continued)

OTHER PUBLICATIONS

European Patent Office; Search Report in International Patent Application No. PCT/CZ2014/000163 dated Jun. 25, 2015; 6 pages.
(Continued)

*Primary Examiner* — Scott Getzow
(74) *Attorney, Agent, or Firm* — Wood Herron & Evans LLP

(57) ABSTRACT

A method of measuring and analyzing the ultra high frequency EKG is performed by measuring the EKG within the frequency range above 250 Hz with a dynamic range of at least 100 dB. In the UHF EKG signal positions of $R_m$ of R wave in QRS complex of EKG are detected on the time axis and the EKG signal is converted to amplitude or power envelopes, the amplitude or power envelopes frequency range is anywhere within the limits from 0.2 Hz to at least 500 Hz. From these envelopes the amplitude and time numerical parameters that describe the myocardium depolarization inhomogeneity and electric myocardium dyssynchrony are determined, and these parameters are used for selecting the patients for multi-chamber stimulators implementation and optimization of their setting.

18 Claims, 17 Drawing Sheets

(51) Int. Cl.
    *A61B 5/02*         (2006.01)
    *A61B 5/0428*     (2006.01)
    *A61B 5/0456*     (2006.01)
    *A61B 5/0472*     (2006.01)
    *A61B 5/044*      (2006.01)
    *A61B 5/0408*     (2006.01)

(52) U.S. Cl.
    CPC ........ *A61B 5/04017* (2013.01); *A61B 5/0428* (2013.01); *A61B 5/0456* (2013.01); *A61B 5/0472* (2013.01); *A61B 5/04286* (2013.01); *A61B 5/4884* (2013.01); *A61B 5/7203* (2013.01); *A61B 5/7225* (2013.01); *A61B 5/7246* (2013.01); *A61B 5/7253* (2013.01); *A61B 5/7415* (2013.01); *A61B 5/04085* (2013.01); *A61B 5/7282* (2013.01)

(56) References Cited

FOREIGN PATENT DOCUMENTS

| WO | 03082077 A2 | 10/2003 |
|----|-------------|---------|
| WO | 2005104937 A2 | 11/2005 |
| WO | 2008015683 A2 | 2/2008 |
| WO | 2009077915 A1 | 6/2009 |

OTHER PUBLICATIONS

European Patent Office; Written Opinion in International Patent Application No. PCT/CZ2014/000163 dated Jun. 25, 2015; 9 pages.

Jurak Pavel et al.; Publication entitled "Ultra-High Frequency ECG Measurement"; Computing in Cardiology 2013, 20130922 n/a— ISSN 2325-8861 ISBN 978-1-4799-0884-4; ISBN 1-4799-0884-3; pp. 783-786.

Guy Amit et al.; Publication Entitled "High-Frequency QRS Analysis in Patients With Acute Myocardial Infarction: A Preliminary Study"; Annals of Noninvasive Electrocardiology, Mar. 1, 2013 Futura Pub., Armonk, US—ISSN 1082-720X; vol. 18, Nr:2, pp. 149-156.

Gerard Faugere et al.; Publication Entitled "Characterization of the Spatial Distribution of Late Ventricular Potentials by Body Surface Mapping in Patients With Ventricular Tachycardia" dated Dec. 1, 1986; pp. 1323-1333.

stim on, VV delay 20 ms stim on, VV delay 60 ms

METHOD OF EKG SIGNAL PROCESSING AND APPARATUS FOR PERFORMING THE METHOD

CROSS-REFERENCE TO RELATED APPLICATIONS

This application is a 371 national stage application of PCT/CZ2014/000163 filed Dec. 19, 2014, which claims priority to Czech Republic Application No. PV 2014-351 filed May 22, 2014, and Czech Republic Application No. PV 2013-1052 filed Dec. 20, 2013, the disclosures of which are hereby incorporated by reference herein in their entirety.

TECHNICAL FIELD OF THE INVENTION

The present invention relates to a method of EKG signal processing and an apparatus for performing the method

DESCRIPTION OF RELATED ART

Apparatuses for recording electric activity of heart, electrocardiogram or EKG, are commonly used in cardiology for heart diseases diagnostic. Standard EKG monitors provide signal in a frequency range up to about 100 Hz. Sensitive high resolution EKG monitors referred to as HD EKG or HF EKG monitors with higher sampling rate up to 4 kHz occur on the market in a limited extent. Frequency range up to 250 Hz is used on these devices. Many publications have indicated that in this frequency range, exclusively in QRS complex area, higher amplitudes of high frequency signal appear—Goldberg A L et al 1981, Petterson J et al 2000, Schlegel T T et al 2004. State of technology and of a high frequency EKG analysis is synoptically described in the article of Guy Amit, et al. 2014. Different form of the QRS complex in the band from 150 up to 250 Hz, i. e. centralization, conceivably broadening and bifurcation of frequency peaks, often defined by means of RAZ (Reduced Area Zone) parameters, serves for a diagnostic of pathological phenomena in myocardium, first of all of ischemic heart disease.

Limited frequency range and limited dynamics of the measured EKG signal, that do not enable subsequent analysis and interpretation of the high frequency electrical activities in the frequency range above 250 Hz, are the limitation of the current HF EKG monitors. The current limitation consists not only in an EKG measuring technique but also in a method of ultra high frequency EKG signals processing and interpretation.

It is the object of the present invention to define an apparatus for measuring ultra high frequency oscillations generated by myocardium UHF EKG, i. e. the frequency range above or way above 250 Hz, and to determine a method of processing the ultra high frequency electrical activity of the myocardium. By means of the UHF EKG apparatus and the method of processing the measured UHF EKG signal it is possible to diagnose various heart abnormalities, pathologies, and determine risks of a sudden cardiac death in a simple and non-invasive way. The present invention also enables so far unknown interpretation of the measured electrical activity of the myocardium. The ultra high frequency oscillations, measurable by means of the present invention, provide information on time and location of an activation of a depolarization phase of action potential of contractile cells predominantly of the left and the right myocardium ventricle.

SUMMARY OF THE INVENTION

The object mentioned above is achieved with the method of the EKG signal processing, the substance of which consists in selecting a frequency range above the frequency of 250 Hz on the EKG signal in measuring channels; from this EKG signal component in the selected frequency range, amplitude or power envelopes of the EKG signal are calculated, which envelopes are averaged with respect to $R_m$ of R wave position to increase a signal-to-noise ratio in a corresponding channel, after which the averaged amplitude or power envelopes of the EKG signal from individual channels are compared on the time axis. From the averaged amplitude or power envelope of the EKG signal advantageously for noise background removal, a median or a mean value is deducted within the range of at least 100 ms after the $R_m$ position to 300 ms after the $R_m$ position, whereupon the negative values of the envelopes, after the median or mean value having been subtracted, are set to zero.

In an advantage embodiment of the invention, the amplitude or power envelopes of the EKG signal are calculated using Hilbert transformation.

In another advantageous embodiment of the invention, the amplitude envelopes of the EKG signal are calculated by the EKG signal filtration, conversion of the signal obtained this way into absolute value and smoothing it.

In still another advantageous embodiment of the invention, the power envelopes of the EKG signal are calculated by the EKG signal filtration, raising the EKG signal to the power of two and smoothing it.

In another advantageous embodiment of the invention, the averaged amplitude or power envelopes of the EKG signal are smoothed within the range from 0 to 5 Hz up to 0 to 200 Hz using low pass filter.

In another advantageous embodiment of the invention, the amplitude or power envelopes of the EKG signal are displayed on a display unit for the averaged amplitude or power envelopes of the EKG signal from individual channels to be compared on the time axis, whereas a colour or a degree of grey is assigned to a displayed signal from each individual channel.

In another advantageous embodiment of the invention, the averaged amplitude or power envelopes of the EKG signal within the interval of 300 ms before and 600 ms after the of R wave position of QRS complex from the individual channels are converted to a series of numerical parameters, where these numerical parameters include amplitude numerical parameters ANPs from a group containing the signal amplitude maximum, the signal power maximum, an integral of the signal amplitude envelope and an integral of the signal power envelope in the individual channels or in sums of the individual channels and in the frequency ranges, and time numerical parameters TNPs from a group containing time positions of the amplitude envelopes maximums, time positions of the amplitude envelopes centres, time positions of the amplitude envelopes beginnings and time positions of the amplitude envelopes ends in the individual channels or in sums of the individual channels and in the frequency ranges. The time position of the amplitude or power beginning in one channel is determined as the first value overrunning a predetermined limit value, the time position of the amplitude or power end in one channel is determined as the last value overrunning the predetermined limit value and the predetermined limit value is determined as a percentage of the amplitude or power maximum, namely within the range of 1 up to 25 percent.

In still another advantageous embodiment of the invention, the numerical parameters are normalized, whereas the numerical parameter P1 for the selected frequency range, the channel or the sum of the EKG signals from several channels is normalized by the second numerical parameter P2 for another frequency range or another channel or another sum of the EKG signals, and whereas the normalized numerical parameter $Pn=P_1/P_2$.

In another advantageous embodiment of the invention, an electric dyssynchrony of ventricles in units of time, defined as a difference between values of the TNPs of the selected EKG channels, and this difference parameter is further used for a selection of patients suitable for multi-chamber stimulator implementation, or with patients with already implemented stimulator for an optimization of the stimulator function setting by shifting the stimulation moments in the heart chambers in relation to each other to reach the minimum absolute value of this parameter.

In still another advantageous embodiment of the invention, with patients with the multi-chamber stimulator first of all the stimulating pulses position on the time axis and their distance D from the TNPs values in the individual channels of the EKG signal in units of time are determined, after which a speed of the stimulating signal transmission into the heart area, that is defined by the EKG channel, is determined on the basis of the distance D and a suitability of the stimulating electrodes positions and characteristics of the electric stimulation in a heart muscle are assessed.

In another advantageous embodiment of the invention, the EKG signal is split into individual frequency ranges within the frequency limits from 0 to 2000 Hz for determining the averaged amplitude or power envelopes of the EKG signal in each individual frequency range. The calculated data are arranged into time-frequency matrices, each row of the matrix is on the time axis at interval from Rm−I to Rm+J, where I and J are time intervals, each in possible range from 50 up to 1500 ms. That way each row of the matrix represents a course of the averaged amplitude or power envelope at interval from Rm−I to Rm+J in the selected frequency range. Frequency ranges of the individual rows of the matrix are shifted in relation to each other. A time course of the frequency power or amplitude in each frequency range is multiplied by a normalization coefficient K according to the function:

$$K=1/(\Sigma(a_i)/n)$$

where n is a number of elements of one matrix row and $a_i$ is ith element of the same row of the matrix, thereby enhancing of low signal powers at higher frequencies is achieved. Time-frequency map after the normalization is advantageously displayed so that degrees of gray scale or colour shades according to the set colour chart are assigned to the individual matrix values.

In another advantageous embodiment of the invention, the amplitude or power envelopes of the EKG signal from the individual channels or a sum of selected channels are converted to a hearable audible signal such that the carrier frequency in the audible frequency range within the limits of 300 to 15000 Hz is modulated by the amplitude or power envelope of the individual channels or the sum of the selected channels, whereas these envelopes are prolonged in time once up to ten times. Alternatively, it is also possible to convert the sum of the amplitude or power envelopes of the channels V1, V2 and V3 and the sum of the amplitude or power envelopes of the channels V4, V5 and V6 of the EKG signal to two hearable audible signals with different carrier frequencies for a stereo reproduction of the ultra high frequency heart activity.

In another advantageous embodiment, the ANPs and TNPs are established for the individual EKG channels to determine the position of pathologic areas of the myocardium, whereas a decrease of the ANPs and an increase of the differences between TNPs indicate an occurrence of the pathologic area of the myocardium in the given EKG channels. In doing so it can be especially advantageous, if the ANPs and TNPs from the EKG channels measured in the course of days, weeks, months and/or years are compared to discover the pathologic progress.

It is also advantageous, if the ANPs and TNPs of the EKG signals obtained in and after physical load tests are evaluated to discover an occurrence of a decreased myocardium oxygenation, whereas a decrease of the ANPs and an increase of the differences between TNPs indicate the decreased myocardium oxygenation during and after the load.

In another advantageous embodiment of the method according to the invention, thereafter EKG maps are used, which EKG maps are simultaneously measured system of the EKG channels arranged in orthogonal coordinates or arranged in another way numbering up to 300 EKG channels, the amplitude or power envelopes and the ANPs and TNPs are determined in all these EKG channels, whereas these parameters are displayed in a three-dimensional matrix, where each matrix element is in accordance with one value of a parameter of one EKG contact, or with one value of the amplitude or power envelope in the same instant of time.

The object mentioned above is achieved also with an apparatus for performing the method described above; a principle of the apparatus will be described hereinafter. The apparatus comprises a block of analogue amplifiers, to the output of which an input of a block of analogue signal to digital signal converters is connected. The individual analogue amplifiers of the block of the analogue amplifiers are connected with their inputs to the outputs of the individual channels of the EKG signal and their outputs are connected to the inputs of the individual converters of the analogue signal to digital signal of the block of the analogue signal to digital signal converters. The whole of a transmission band of the chain of the analogue amplifier block and the block of the analogue signal to digital signal converters has a dynamic range above 100 dB in each recorded channel. A storage unit is connected to the outputs of the individual analogue signal to digital signal converters of the block of the analogue signal to digital signal converters. To the output of the storage unit a detector $R_m$ of the R wave of the QRS complex is connected, to the output of which through a band pass filter a unit for calculating the envelopes and averaging is connected. At least one indicating unit is connected to the output of the unit for calculating the envelopes and averaging.

In an advantageous embodiment of the apparatus according to the invention, the indicating unit is a display unit for displaying the envelopes and/or calculated numerical parameters.

In another advantageous embodiment of the apparatus according to the invention, the indicating unit is an audible signal generator.

DESCRIPTION OF THE DRAWINGS

The invention is explained in details hereinafter by means of figures included in attached drawings, where in FIG. 1 the channel V3 and the power envelopes of the measured EKG signal in various frequency ranges in two consecutive heart beats are depicted.

EXAMPLES OF THE INVENTION IMPLEMENTATION

Figure 1:
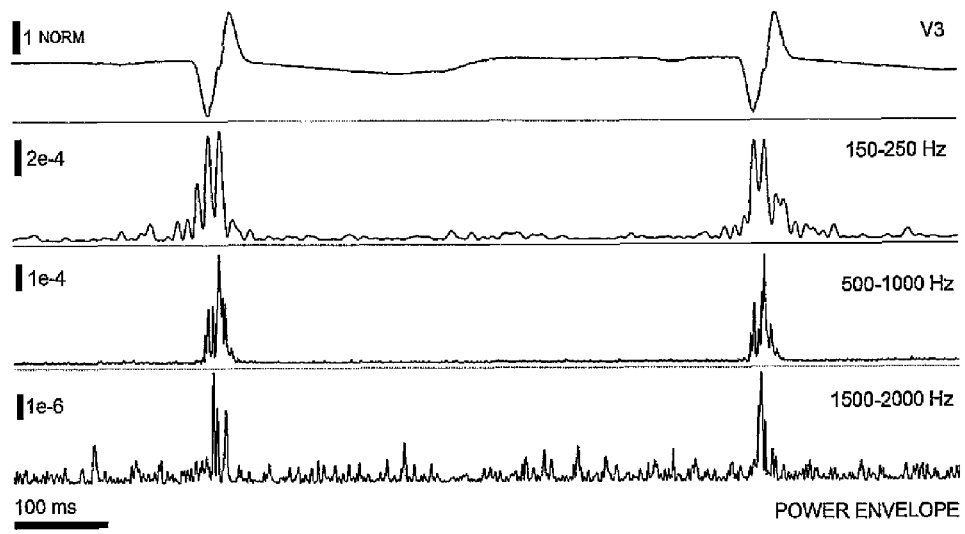
Figure 2:
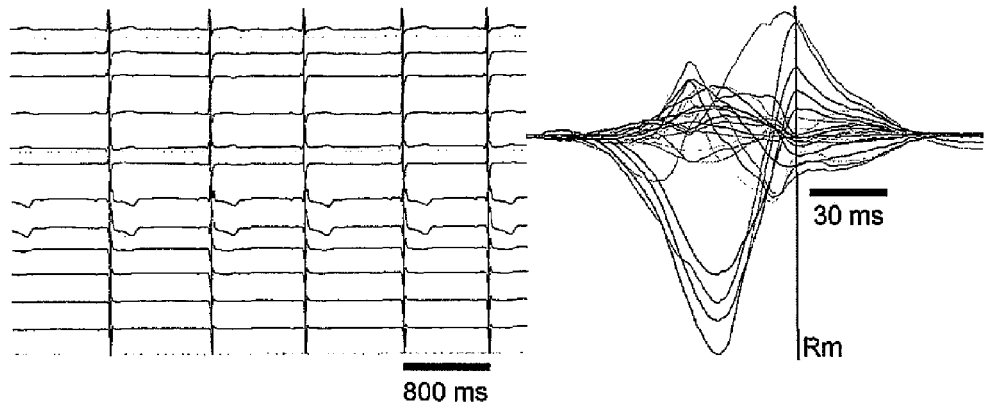
in FIG. 2 the position of $R_m$ of R wave in twelve-lead EKG signal is illustrated.
Figure 3A:
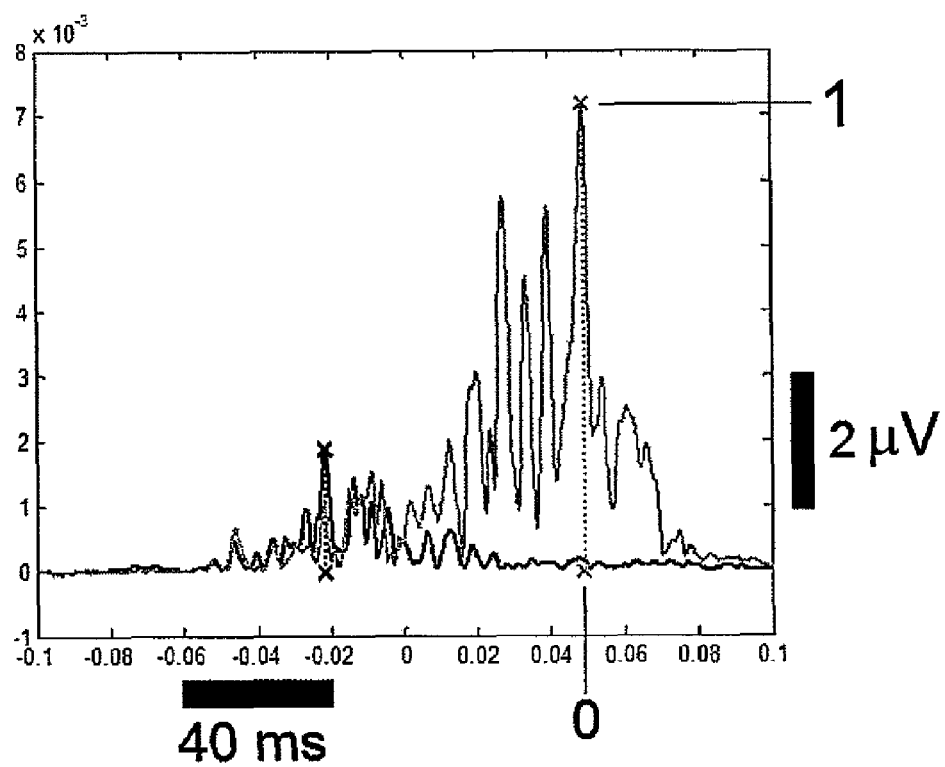
FIG. 3A is an illustration of the averaged amplitude envelopes in micro volts of the twelve-lead EKG signal within the range of 500 up to 1000 Hz.
Figure 3B:
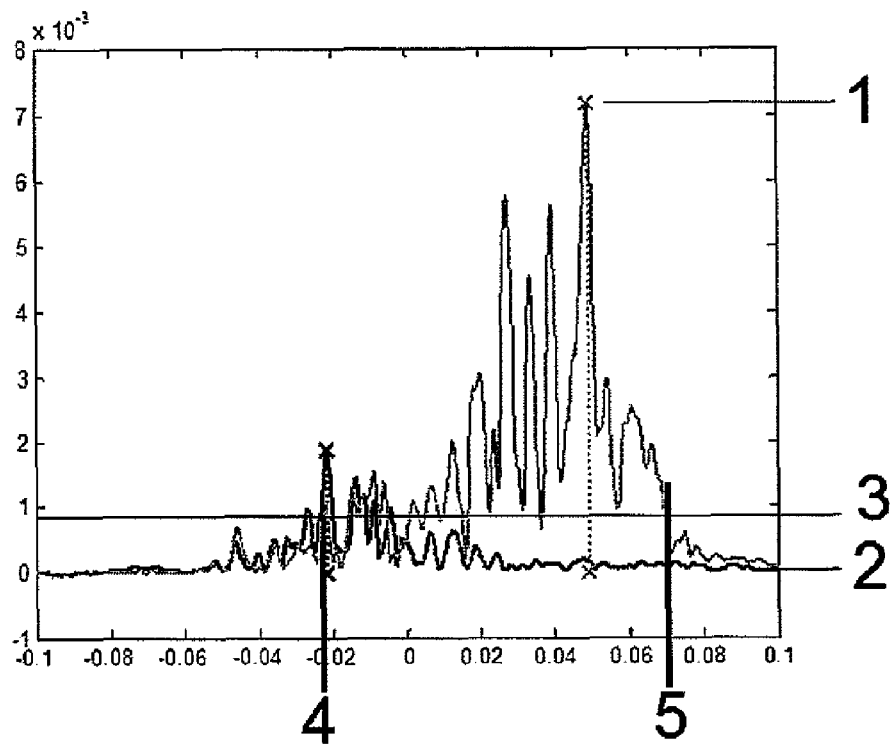
FIG. 3B is an illustration of smoothing the averaged amplitude envelope of the EKG signal of the channels V1 and V6 by means of a low pass filter within the range of 0 to 40 Hz.
Figure 3C:
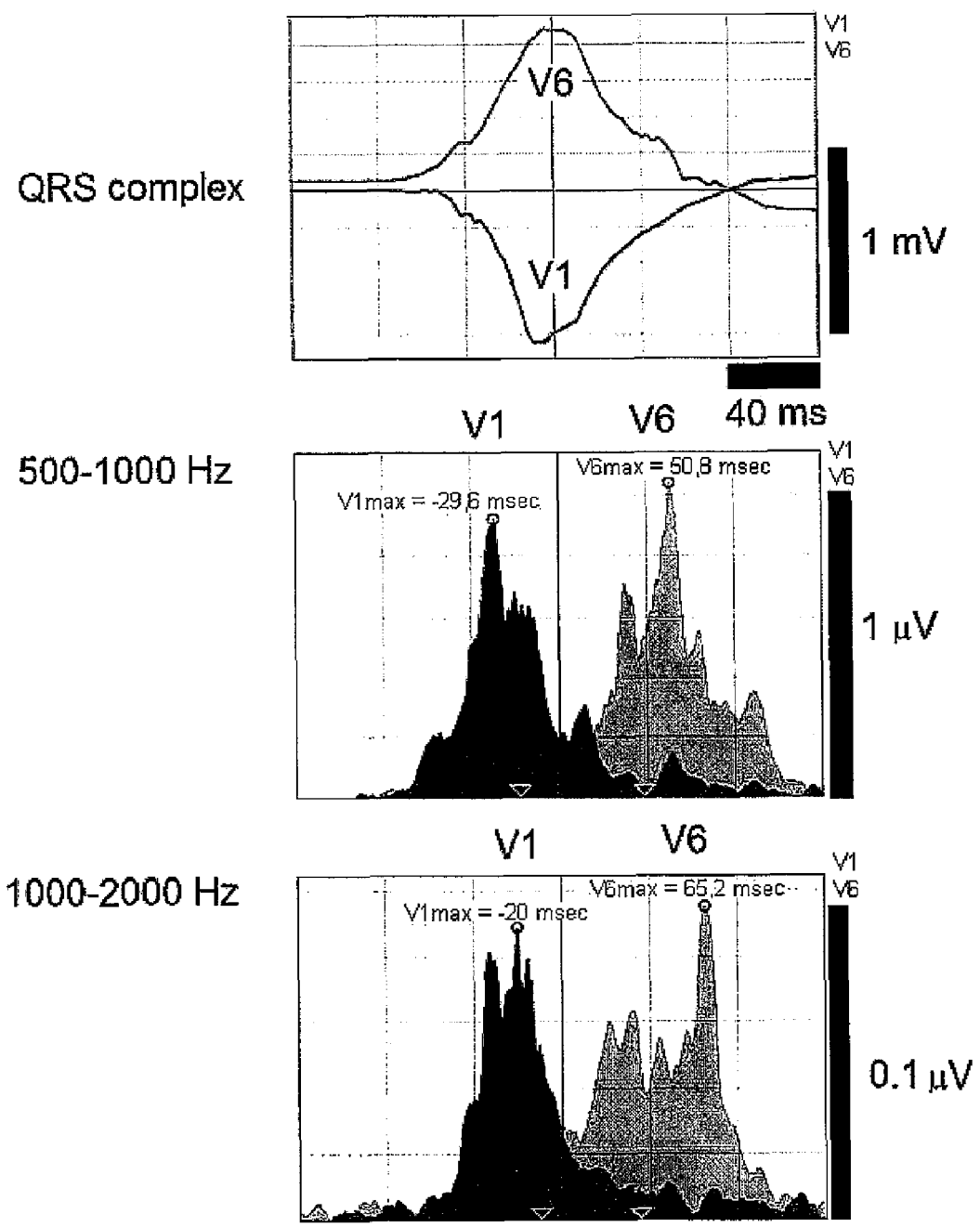
in FIG. 3C there is the EKG signal from FIG. 3B, from above QRS complex of the EKG signal, the envelopes in the range of 500 up to 1000 Hz and the envelopes in the range of 1000 up to 2000 Hz.

The invention relates to the method of measuring and processing of the high frequency activity of the electrocardiogram in selected frequency ranges above the value of 250 Hz and the method of analysing the high frequency oscillation of the electrocardiogram, the most important component of which is that the high frequency oscillation generated by a heart muscle is measured. The EKG signal is scanned by several sensors on a surface of a chest and a back and from these sensors it comes through various channels to the analysis. A frequency range above 250 Hz is selected on the EKG signal in the measuring channels and the amplitude or power envelopes of the EKG signal in the selected frequency range are calculated. In FIG. 1 the power envelopes of the measured EKG signal lead V3 in ranges of 150 up to 250 Hz, which is a common range for HF EKG, 500 up to 1000 Hz and 1500 up to 2000 Hz, beat by beat. The range of 500 up to 1000 Hz shows a considerably better in detail depicted morphology and time delimitation of the power envelopes in the QRS complex area then the lower range of 150 up to 250 Hz. But in fact it is a case of the EKG signal that is not averaged and is displayed beat by beat. In FIG. 2 the $R_m$ of R wave position in the twelve-lead EKG signal is depicted. For determination the $R_m$ of R wave position it is important for it to be in the same position in all consecutive R waves of the EKG signal, which ensures a synchrony for averaging. The amplitude or power envelopes of the EKG signal are calculated by means of Hilbert transformation or by filtration, raising the EKG signal to the power of two and smoothing. FIG. 3 is a demonstration of the amplitude envelopes in micro volts of the twelve-lead EKG signal. In this case it is an average of 846 heart beats and the individual envelopes from the twelve-lead EKG are depicted one over the other. A demonstration of smoothing the averaged amplitude envelope of the EKG signal of the channel V1 (marked with dark grey colour) and the channel V6 (marked with light grey colour) by means of a low pass filter in the range of 0 to 40 Hz is shown in FIGS. 3B and 3C. The smoothing and the number of depicted leads reduction enable better arranged identification of the envelopes from the selected leads. The mode of representation in FIGS. 3B and 3C, where dark grey colour corresponds to the lead V1 and light grey colour corresponds to lead V6, enables an advantageous identification of a dyssynchrony of the right ventricle, the septum and the lateral wall of the left ventricle of the myocardium. The amplitude envelope of the lead V1 precedes the amplitude envelope of the lead V6, this situation being interpreted as an earlier occurrence of an electric depolarization in the septum and the right ventricle before the electric depolarization occurrence in the lateral wall of the left ventricle.

Figure 4A:
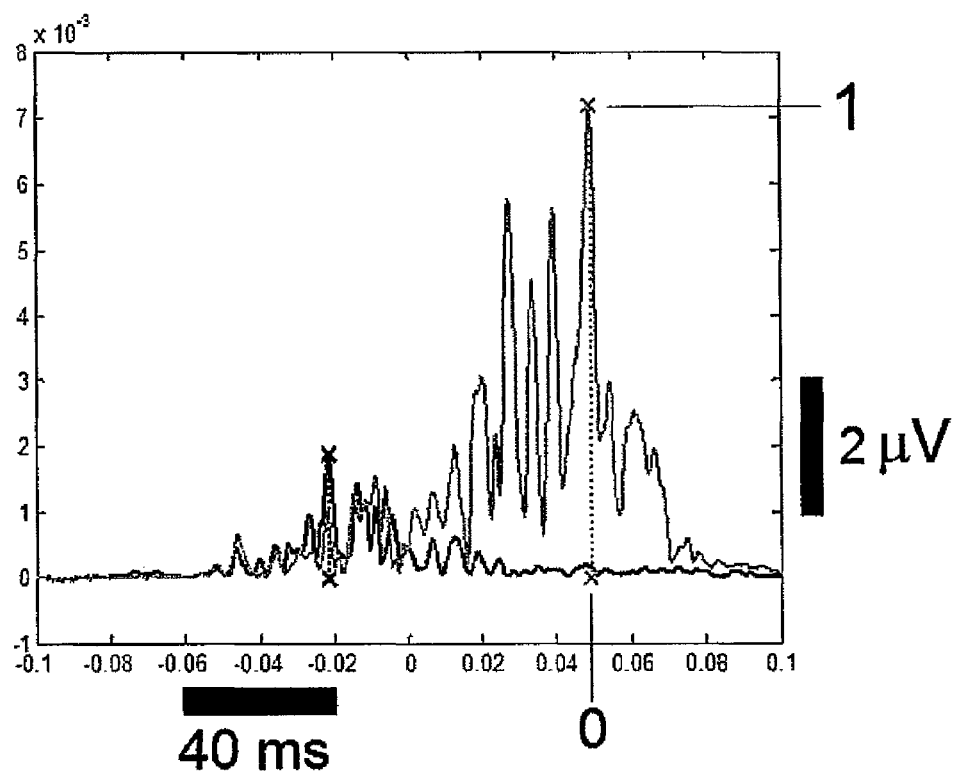
in FIG. 4A a detection of maximums and their time positions of the averaged amplitude envelopes of two different EKG channels is illustrated, 0—maximum position on the time axis, 1—maximum value, and in FIG. 4B a detection of time positions of the amplitude beginning and end on one EKG channel, 1—maximum, 2—zero line, 3—horizontal line on the level of 10 percent of the maximum, 4—the amplitude beginning, 5—the amplitude end for the signal marked with light grey.
Figure 4B:
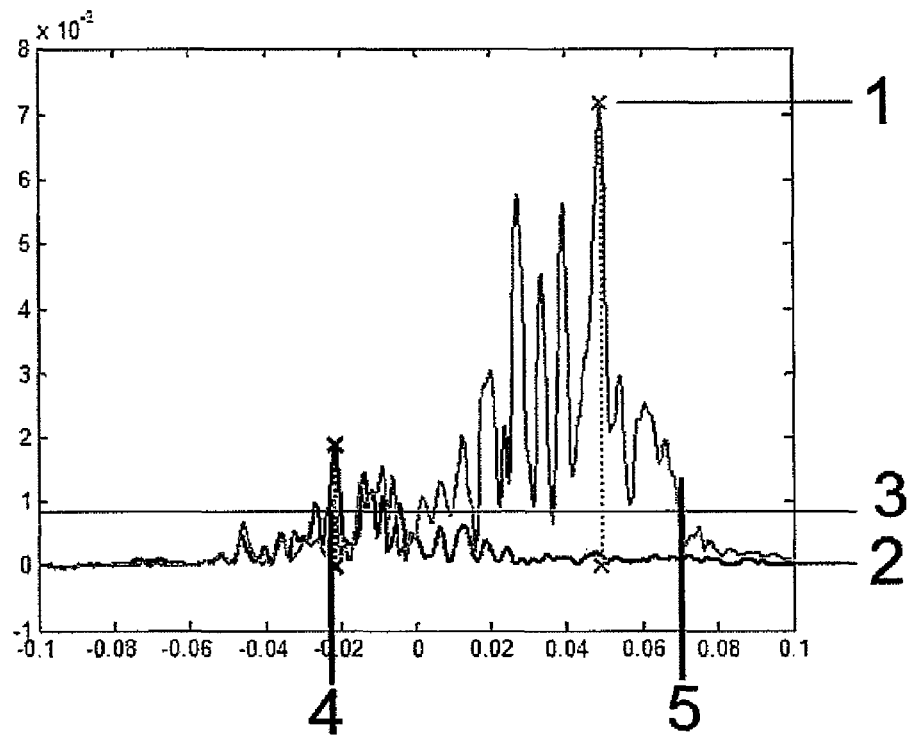
Figure 5:
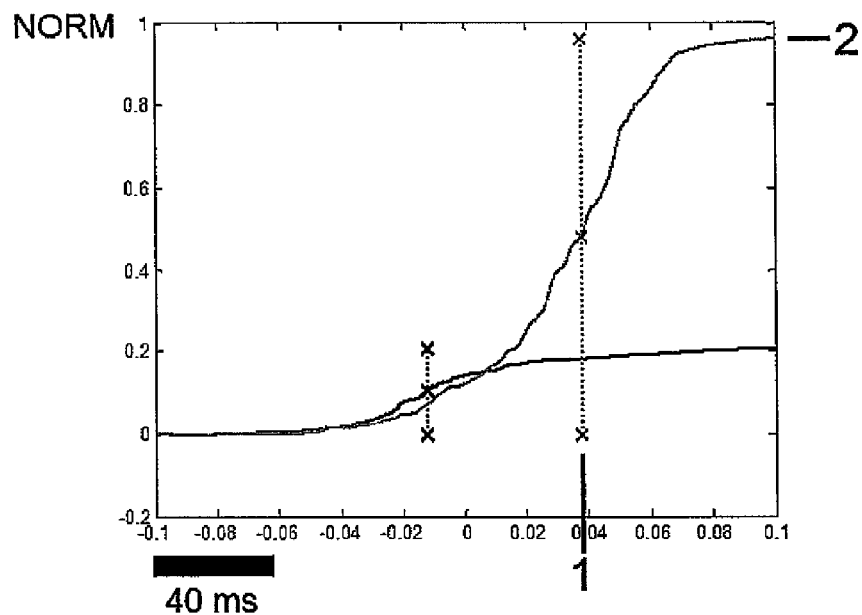
in FIG. 5 a detection of positions and values of integral sums of the amplitude envelopes from FIG. 4, digit 1 shows the centre position in a half of the integral value and digit 2 shows the integral value.

Alternatively the averaged amplitude or power envelopes of the EKG signal from the individual channels can be converted to a series of numerical parameters defining amplitudes, powers and their time distribution in the individual channels or in sums of the EKG signals from the individual channels. In doing so the numerical parameters including amplitudes or powers in the individual channels or in the sum of the selected channels and in the individual frequency ranges are calculated as maximums or integral sums in a selected period of time at interval of 300 ms before and 600 ms after the $R_m$ of R wave position of QRS complex. In FIG. 4A a detection of the maximums and their time positions of the averaged amplitude envelopes within the range of 500 up to 1000 Hz of two different EKG channels is illustrated, 0—maximum position, 1—maximum value. In FIG. 4B a detection of the time positions of the amplitude beginning and end of the EKG channel marked with light grey colour is depicted, 1—maximum, 2—zero line, 3—horizontal line at the level of 10 percent of the maximum, 4—beginning of the amplitude marked with light grey colour, 5—end of the amplitude marked with light grey colour. In FIG. 5 a detection of centres positions and values of the integral sums of the amplitude envelopes within the range of 500 up to 1000 Hz of two different EKG channels from FIG. 4 is illustrated, 1—the centre of the EKG channel marked with light grey colour determined in a half of the value of the integral sum marked with 2.

Furthermore the numerical parameters can be normalized. The normalization enables comparison of numerical parameters from various leads, from various frequencies or even from various measurements of one or more subjects. The process proceeds in such a way, that the numerical parameters defining amplitudes, powers and their time distribution are used, where the parameter P1 for the selected frequency range, the channel or the sum of the EKG signals from several channels is normalized by the second parameter P2 for another frequency range or another channel or another sum of the EKG signals. The normalized parameter is $P_n=P_1/P_2$, where $P_n$ is the normalized parameter, $P_1$ is the parameter in the first frequency range and $P_2$ is the parameter in the second frequency range.

Figure 6:
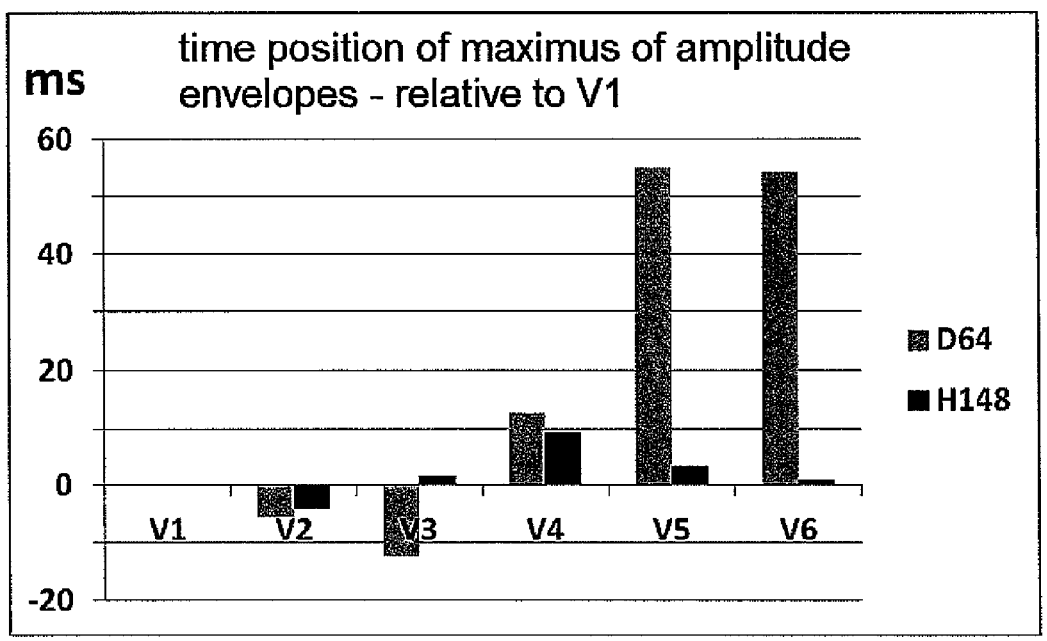
in FIG. 6 maximum time positions for the individual channels of a healthy volunteer H148 and of a patient D64 with a diagnosed blockade of the left Tawara bundle branch are depicted side by side, channel V1 position was set to zero, thus the other positions are relative in relation to the channel V1 position.
Figure 7:
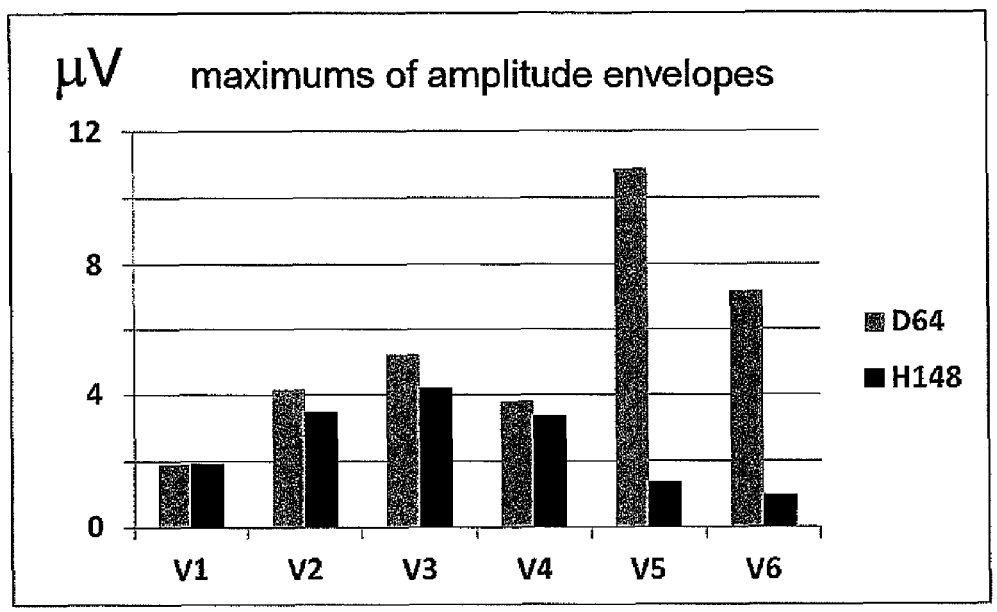
in FIG. 7 values of maximums of the amplitude envelopes for the individual channels from FIG. 6 are depicted side by side.

The numerical parameters can be depicted in a diagram, where the individual channels, i. e. V1, V2, V3, V4, V5 and V6 are on the x-axis and amplitudes or powers or time distribution of the amplitudes or powers are on the y-axis. Exemplary measurements of the EKG signal provided the following results:

In FIG. 6 the time positions of the amplitude envelopes maximums within the range of 500-1000 Hz in milliseconds for the individual channels of a healthy volunteer H148 and of a patient with diagnosed blockade of the left bundle D64 are depicted. In FIG. 7 the values of the amplitude envelopes maximums in millivolts for the individual channels of the same healthy volunteer H148 and the same patient with diagnosed blockade of the left bundle D64 are depicted side by side.

For practical use of the method for the EKG signal processing it proved to be advantageous, when the amplitude or power envelopes of the individual channels or the sum of the selected channels were converted to a hearable audio signal in such a way, that the carrier frequency in the audible frequency range of 300 up to 15000 Hz was modulated by the amplitude or power envelope of the individual channels or the sum of the selected channels, whereas these envelopes were prolonged once up to ten times in the time area.

Figure 8:
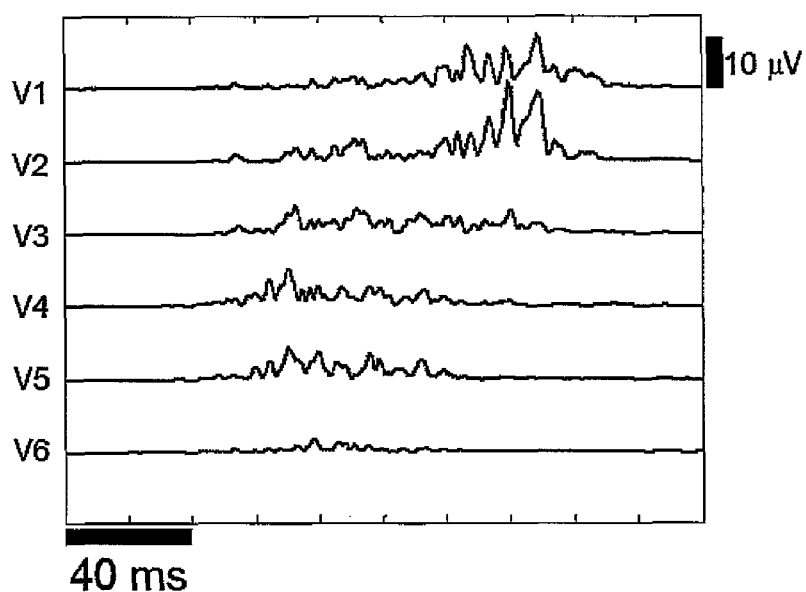
in FIG. 8 the amplitude envelopes for the individual channels V1, V2, V3, V4, V5 and V6 are depicted.
Figure 9A:
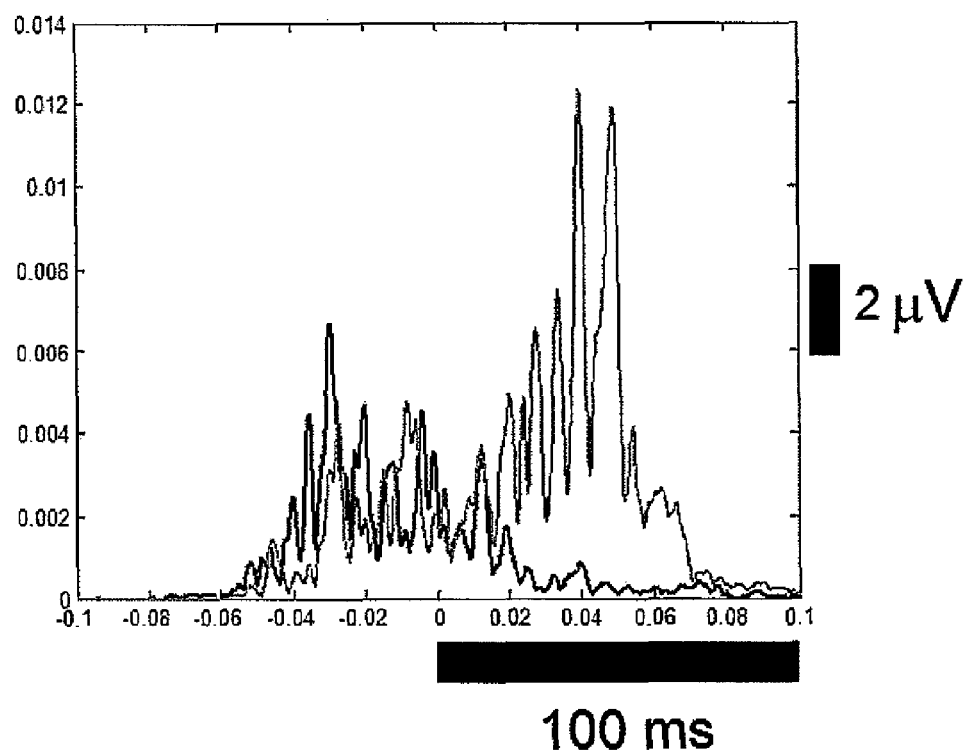
in FIG. 9A the channels from FIG. 8 are depicted, namely combined channels V1, V2 and V3 marked with dark grey colour and combined channels V4, V5 and V6 marked with light grey colour.
Figure 9B:
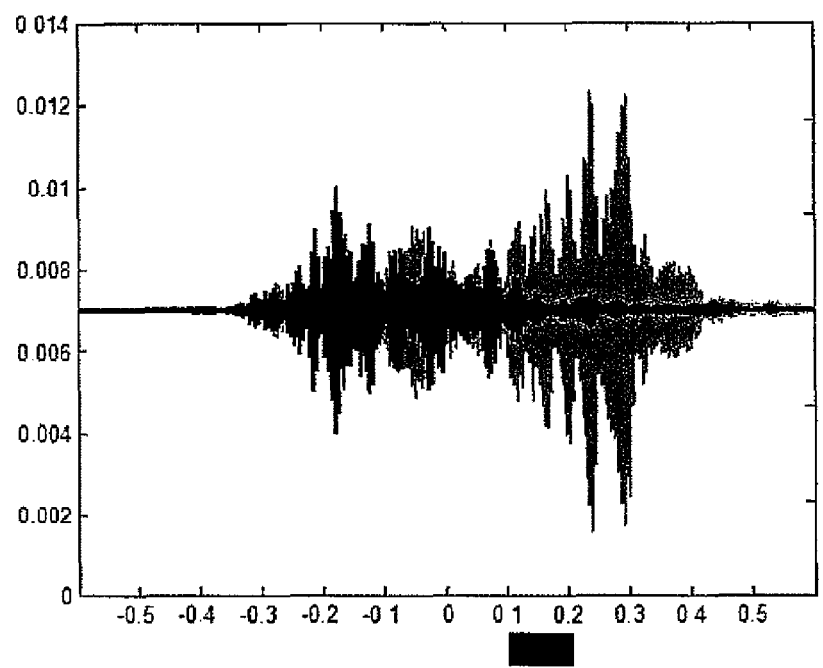
in FIG. 9B there is a sum of the amplitude envelopes, after the time axis having been spread eight times, modulating carrier frequency 1 kHz—marked with dark grey colour, and 2 kHz—marked with light grey colour.

It proved to be especially practical for instance a conversion of the sum of the amplitude or power envelopes of the channels V1, V2 and V3 and the sum of the amplitude or power envelopes of the channels V4, V5 and V6 to two hearable audio signals with different carrier frequencies, which resulted in a stereophonic reproduction of the ultra high frequency heart activity. In FIG. 8 the amplitude envelopes for the individual channels V1 to V6 in the frequency range of 500-1000 Hz are depicted. In FIG. 9A the amplitude envelopes of the sum of the channels V1, V2 and V3 are marked with dark grey colour and the envelopes of the sum of the channels V4, V5 and V6 are marked with light grey colour. These envelopes modulate the carrier frequency 1 kHz—darker shade of grey in FIG. 9B and the carrier frequency 2 kHz—lighter shade of gray. The time axis in FIG. 9B is eight times spread when compared with FIG. 9A. And so the resulting modulated audio signal does not take only 100 ms but it takes 800 ms, which is the period suitable for being registered by human hearing.

Figure 10:
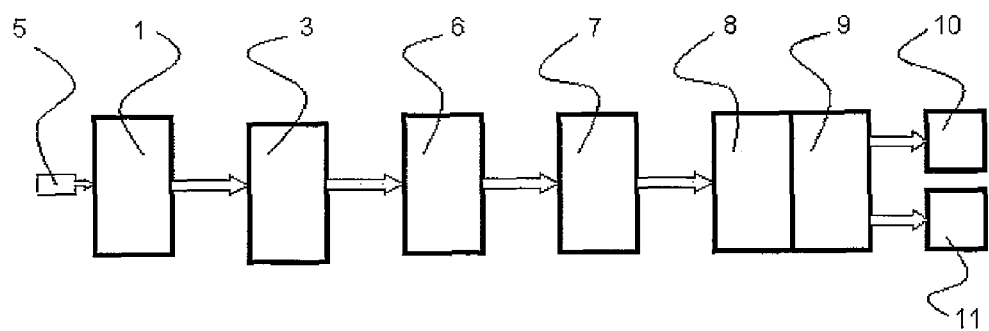
in FIG. 10 the apparatus for performing of the method according to the invention is depicted.

The apparatus for performing the method described above is illustrated in FIG. 10. Here is a block 1 of analogue amplifiers, to the output of which the input of a block 3 of analogue signal to digital signal converters is connected. The block 1 of the analogue amplifiers is connected with its input to outputs of individual sensors 5 of the EKG signal. The chain of the sensors 5 of the block 1 of the analogue amplifiers and the block 3 of the analogue signal to digital signal converters has a dynamic range above 100 dB in the whole transmission band. To the output of the block 3 of the analogue signal to digital signal converters a storage unit 6 is connected, to the output of which a detector 7 of the $R_m$ of R wave of QRS complex is connected. To the output of the detector 7 of the $R_m$ of R wave of the QRS complex through a band pass filter 8 a unit 9 for computing envelopes and averaging is connected, to the outputs of which indicating units are connected. These indicating units are a display unit 10 for displaying the envelopes and/or the calculated numerical parameters and a generator 11 of audio signal.

Figure 11:
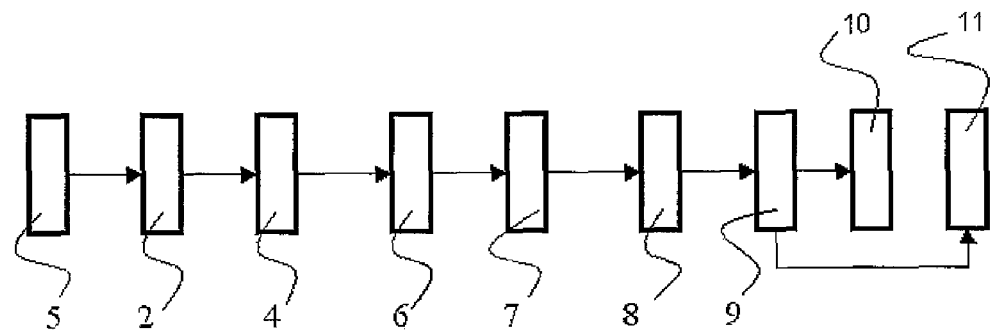
in FIG. 11 a path of the EKG signal from one sensor to the display unit for displaying the envelopes and/or the calculated numerical parameters, and to the audible signal generator is illustrated; in upper part of the FIG. 12 the courses of the QRS complex of channels V1 and V6, and in lower part of the figure the smoothed amplitude envelopes within the range of 500-1000 Hz, for the channel V1 marked with dark grey colour and for the channel V6 marked with light grey colour, are depicted for a normal healthy heart FIG. 12A, for a heart with a delayed activation of the left ventricle FIG. 12B and for a heart with delayed activation of the right ventricle and part of the septum FIG. 12C.

In FIG. 11 a path of the EKG signal from one sensor 5 to the display unit 10 for displaying the envelopes and/or the calculated numerical parameters and to the generator 11 of the audio signal is depicted. From each used sensor 5 the EKG signal goes through a separate channel as far as the unit 9 for computing envelopes and averaging, where a superposing of the signals from the individual sensors 5 can occur according to requirements of a device operator. The sensor 5 of the EKG signal is connected to the analogue amplifier 2, to the output of which the input of the analogue signal to digital signal converter 4 is connected. To the output of the analogue signal to digital signal converter 4 the storage unit 6 is connected, to the output of which the detector 7 of the $R_m$ of R wave of the QRS complex is connected. To the output of the detector 7 of the $R_m$ of R wave of the QRS complex through a band pass filter 8 the unit 9 for the envelopes computing and averaging is connected, to the outputs of which the display unit 10 for displaying the envelopes and/or the calculated numerical parameters and the generator 11 of the audio signal are connected.

In the digitalized EKG signal characteristics of very weak high frequency oscillations of the EKG signal are analysed. Voltage levels of those signals are so low and on so high frequencies, that neither common EKG apparatuses nor the high frequency EKG or the EKG with high resolution are able to record either detect them in sufficient quality. For an evaluation of particular heart activities the $R_m$ of R wave position in the QRS complex of EKG is detected. A demonstration of the $R_m$ position in the twelve-lead EKG signal is in FIG. 2. On the left side of FIG. 2 a course of the EKG signal from the individual sensors 5 is depicted on the time axis, whereas the scanned voltage is on the vertical axis and the scanned time is on the horizontal axis. The distance between two adjacent $R_m$ positions is approximately 0.8 s. One $R_m$ position is then enlarged on the right side of FIG. 2, whereas the signals from the individual sensors 5 are superimposed one on top of the other. The time interval here is about ±80 ms. The EKG signal is further processed in such a way that the signals from the individual sensors 5 are converted to the amplitude or power envelopes. The amplitude or power envelopes frequency range is selected anywhere within the range from 0.2 Hz to the transmission bandwidth of the UHF EKG apparatus, it means for instance within the ranges of 0.2-80 Hz, 250-500 Hz, 500-000 Hz, 500-1500 Hz, 1500-2000 Hz and others.

For the calculation of the amplitude or power envelopes within the defined frequency range a procedure using Hilbert transformation or a procedure using a filtration can be used with subsequent raising the EKG signal to the power of two and smoothing. A demonstration of the UHF EKG signal for the channel V3 and of the power envelope within the ranges of 150-250 Hz, 500-1000 Hz and 1500-2000 Hz is shown in FIG. 1.

To increase the signal-to-noise ratio of very weak ultra high frequency oscillations, particular amplitude or power envelopes in appropriate frequency range and appropriate channel are averaged according to the detected $R_m$ of R wave position. In doing so, the averaging can be performed alternatively with an exclusion of irregular, pathological and artificial heart beats or on the contrary with a selection of them. With this procedure it is possible to monitor the ultra high frequency oscillation better. Further according to this invention, the amplitude or power envelopes for different EKG signals from the individual sensors 5 are distinguished with different colour shades or degrees of gray for a graphical representation. The graphical representation is made up by particular courses of the amplitude or power envelopes from the EKG channels or their sums. FIG. 3A shows the averaged amplitude envelopes of the EKG signal within the range of 500 up to 1000 Hz, the particular EKG channels are distinguished by shades of grey. FIGS. 3B and 3C show the amplitude envelopes of the EKG signal of the channel V1 (marked with darker gray) and the channel V6 (marked with lighter gray) smoothed by means of a low pass filter within the range of 0 to 40 Hz.

Figure 14:
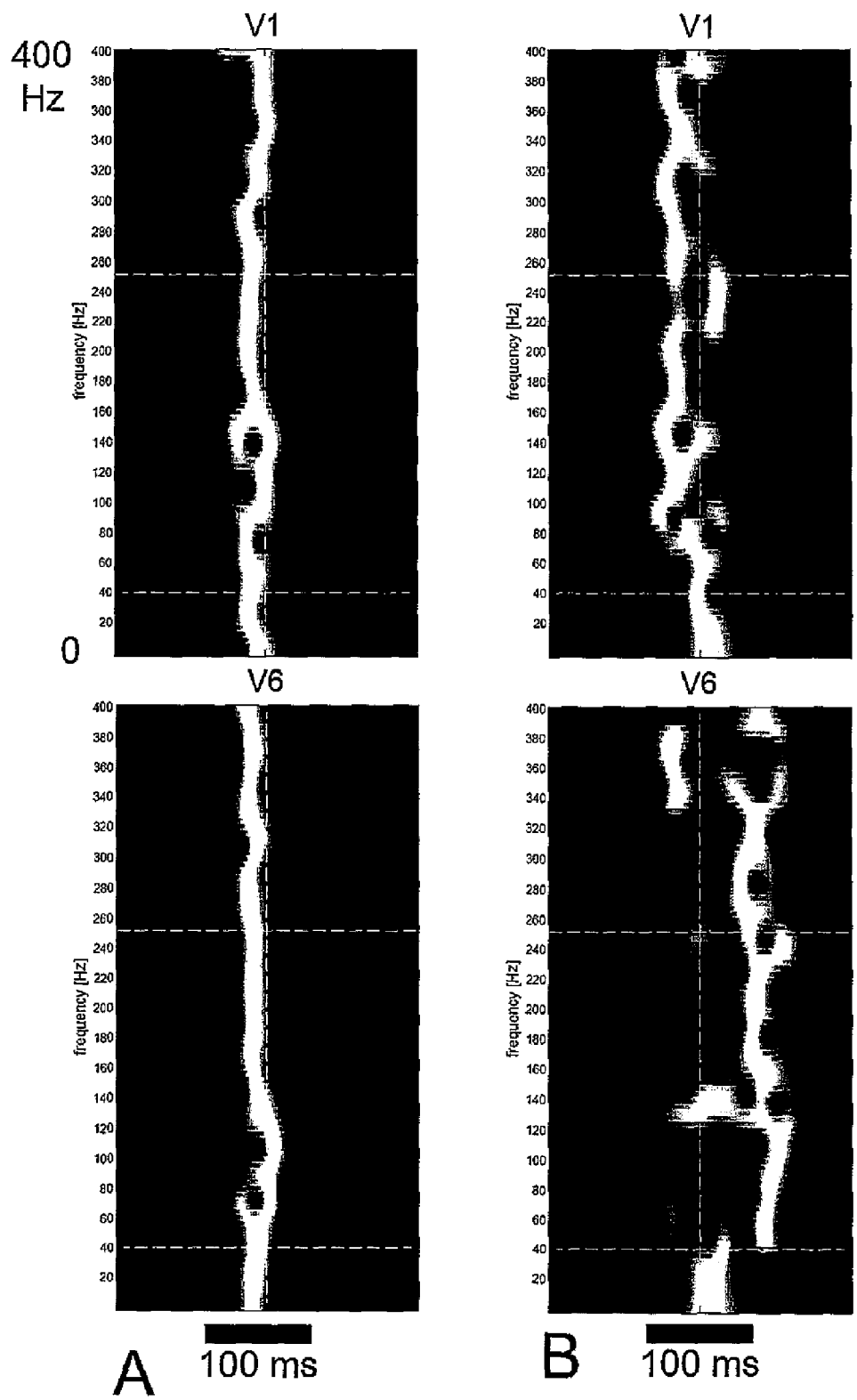
FIG. 14A is a time-frequency map within the range of 0 up to 400 Hz of a healthy subject for the channels V1 and V6, the subject is the same as in FIG. 12A.
FIG. 14B is a time-frequency map of a subject with late activation of the left ventricle, the subject is the same as in FIG. 12B.

Further according to this invention, the EKG signal is divided into consecutive frequency ranges within the frequency limits of 0 to 2000 Hz. In those ranges the averaged amplitude or power envelopes of the EKG signal are determined according to this invention. The calculated data are arranged into time-frequency matrixes, each row of the matrix being on the time axis at interval from Rm−I to Rm+J, where I and J are time intervals, each within the range of 50 up to 1500 ms. And so each matrix row represents a course of the averaged amplitude or power envelope at interval Rm−I to Rm+J in the selected frequency range. For a more advantageous interpretation of the time-frequency matrixes, the time course of a frequency power in each frequency range is multiplied by a normalization coefficient K according to the following function:

$$K=1/(\Sigma(a_i)/n)$$

where n is a number of values of one matrix row and $a_i$ is ith element of the same matrix row, and therethrough enhancement of low powers of the signal on higher frequencies is reached. The time-frequency map after the normalization advantageously is displayed in such a way that degrees of gray or colour shades according to a set colour chart are assigned to the individual matrix values. A demonstration of the time-frequency map is in FIG. 14.

For the amplitude or power envelopes the numerical parameters are further determined, which parameters describe the amplitudes, the powers and their time distribution in the individual EKG signals or in sums of them.

The numerical parameters including the amplitudes and the powers in the individual signals or in the sum of the selected signals in the individual frequency ranges are calculated as maximums or integral sums in the selected period of time within the interval of 300 ms before and 600 ms after the $R_m$ of R wave position of the QRS complex. FIG. 4A shows an example of detection of the maximum from two signals in the delimited interval of 100 ms before the $R_m$ position and 100 ms after the $R_m$ position. FIG. 5 then shows an example of the centre and the integral sum of the amplitude envelope of the same two signals in the delimited interval of 100 ms before the $R_m$ position and 100 ms after the $R_m$ position.

The numerical parameters in one frequency range can be further normalized by the parameters in the second frequency range by formula $P_n=P_1/P_2$, where $P_n$ is the normalized parameter, $P_1$ is the parameter in the first frequency range and $P_2$ is the parameter in the second frequency range. The normalization enables to eliminate different levels of amplification and different characteristics of the sensors 5 scanning the EKG signal.

Figure 12A:
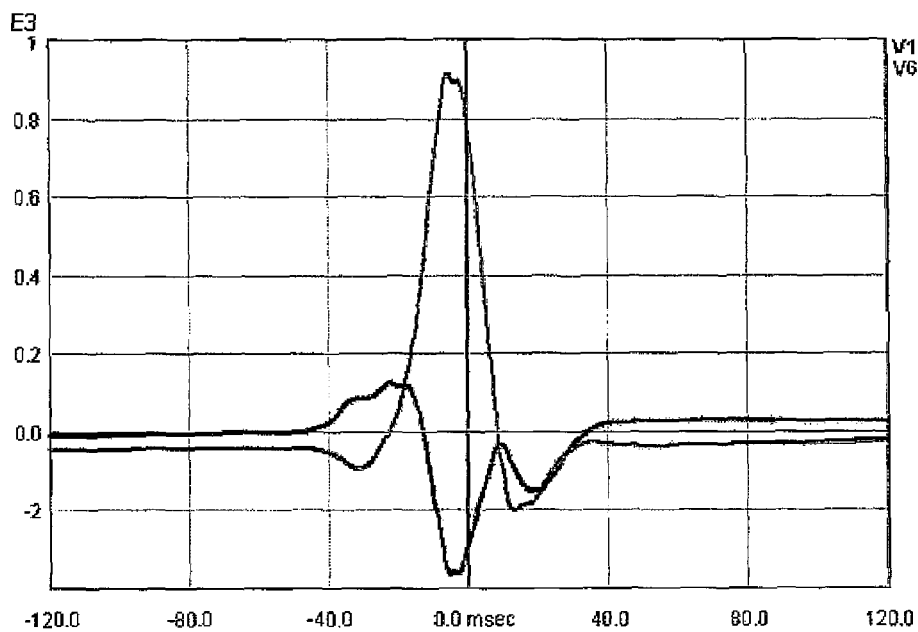
Figure 12A:
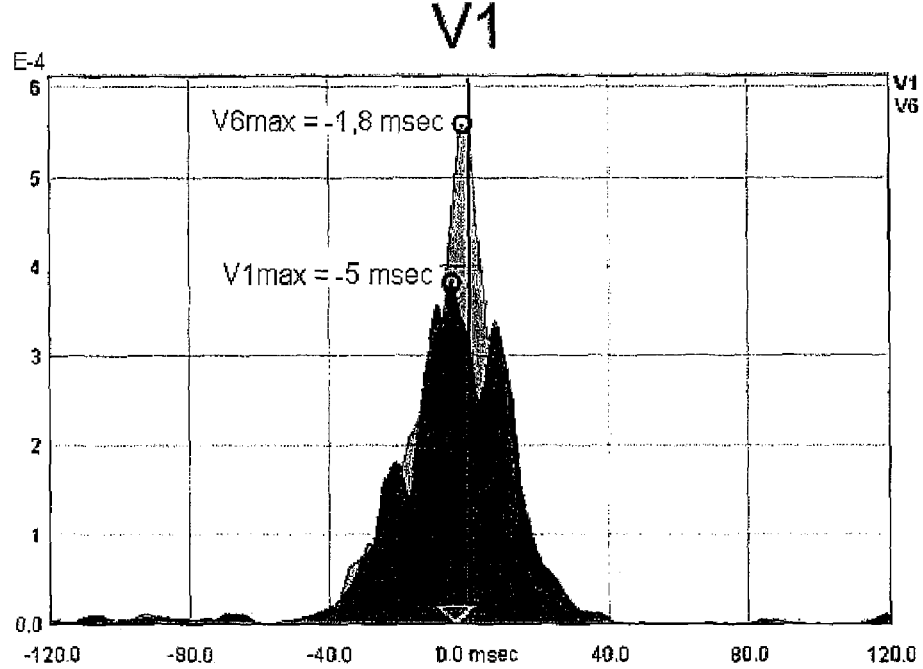
Figure 12B:
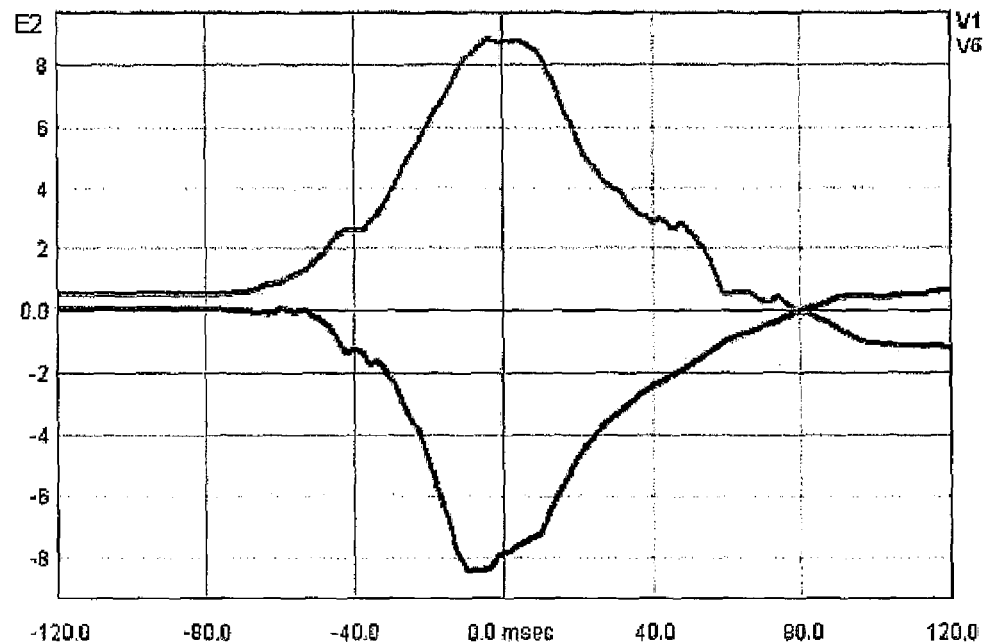
Figure 12B:
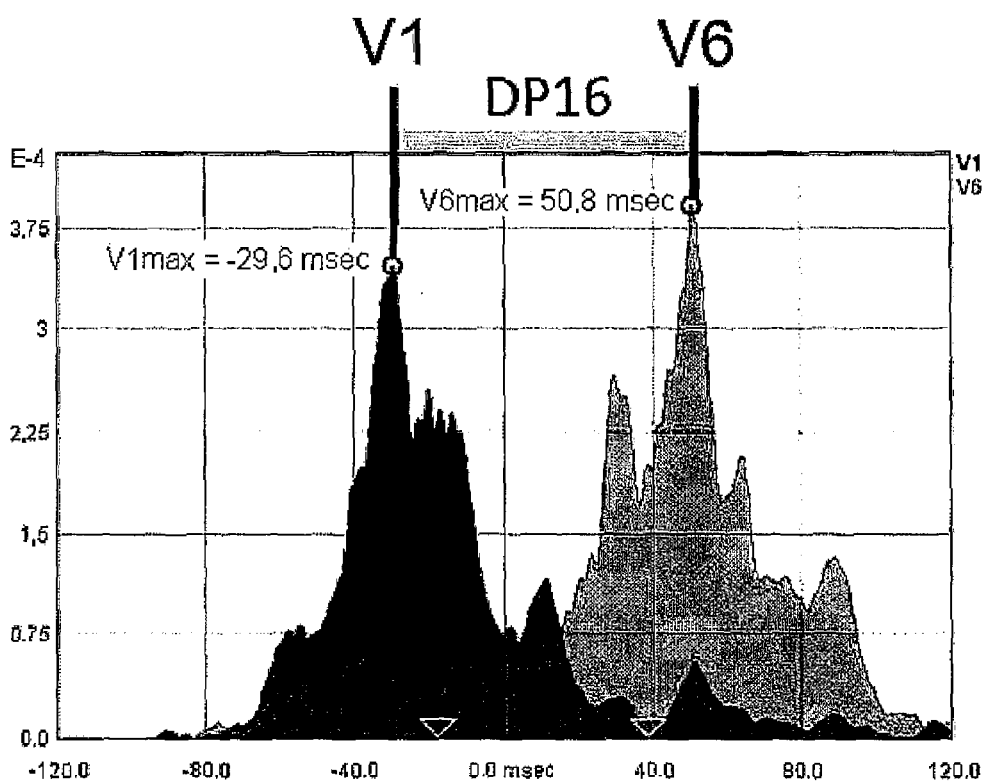
Figure 12C:
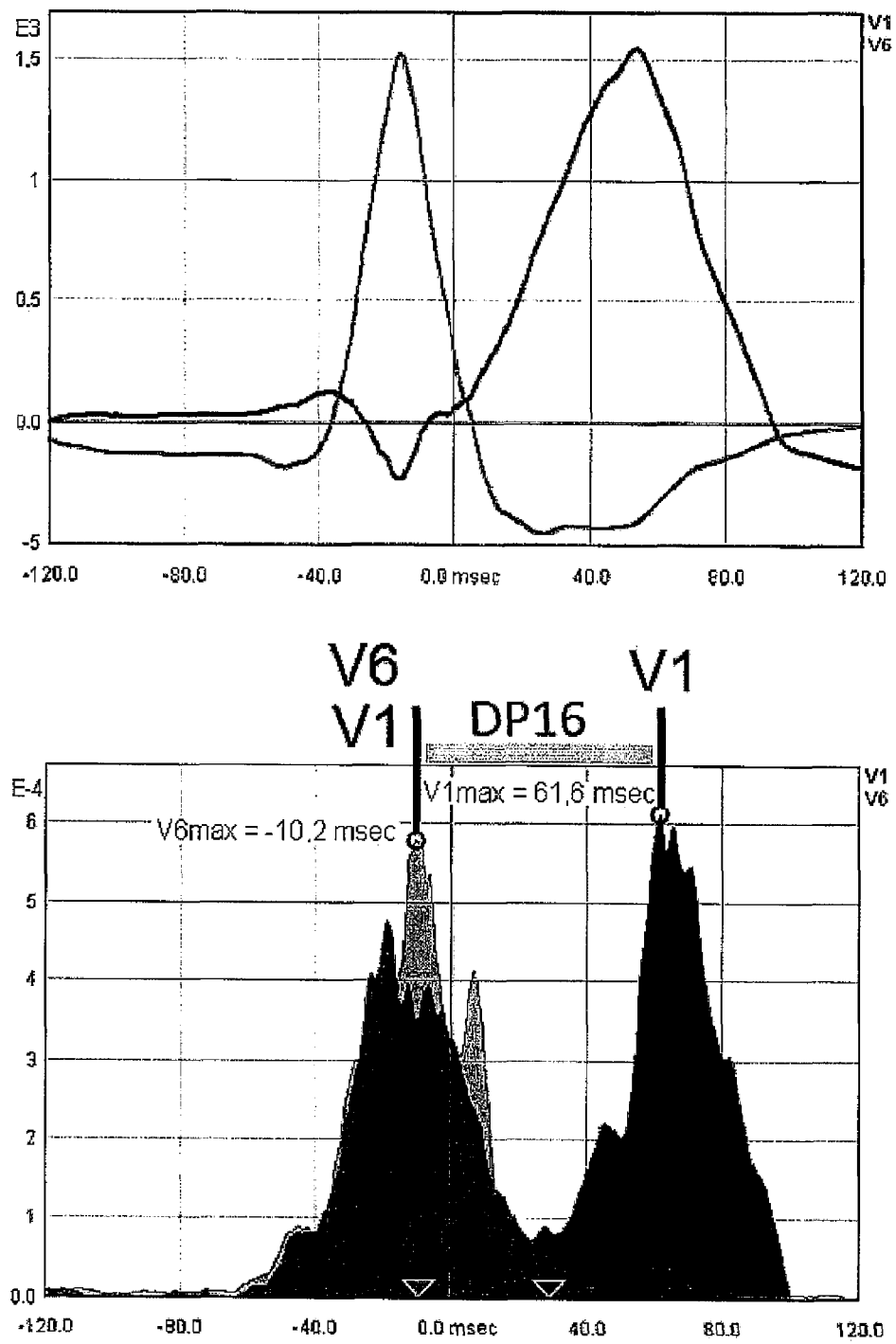
Figure 13A:
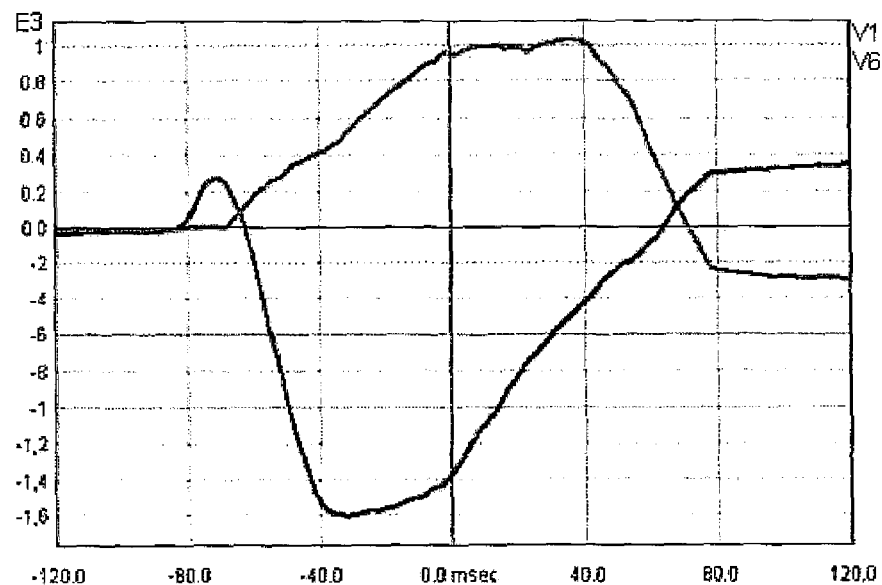
in FIG. 13 an effect of the switched off FIG. 13A and the switched on FIGS. 13B, 13C, 13D and 13E biventricular stimulator is depicted in the same format as in FIG. 12, black vertical lines in FIG. 13 represent positions of stimulating pulses of individual heartbeats included in the average and a light grey vertical column represents the area, in which the effect of the stimulation on the EKG signal was eliminated, in FIG. 13B the left and right ventricles are stimulated in same instant, in FIG. 13C the stimulation of the left ventricle precedes by 20 ms, in FIG. 13D the stimulation of the left ventricle precedes by 40 ms and in FIG. 13E the stimulation of the left ventricle precedes by 60 ms.
Figure 13A:
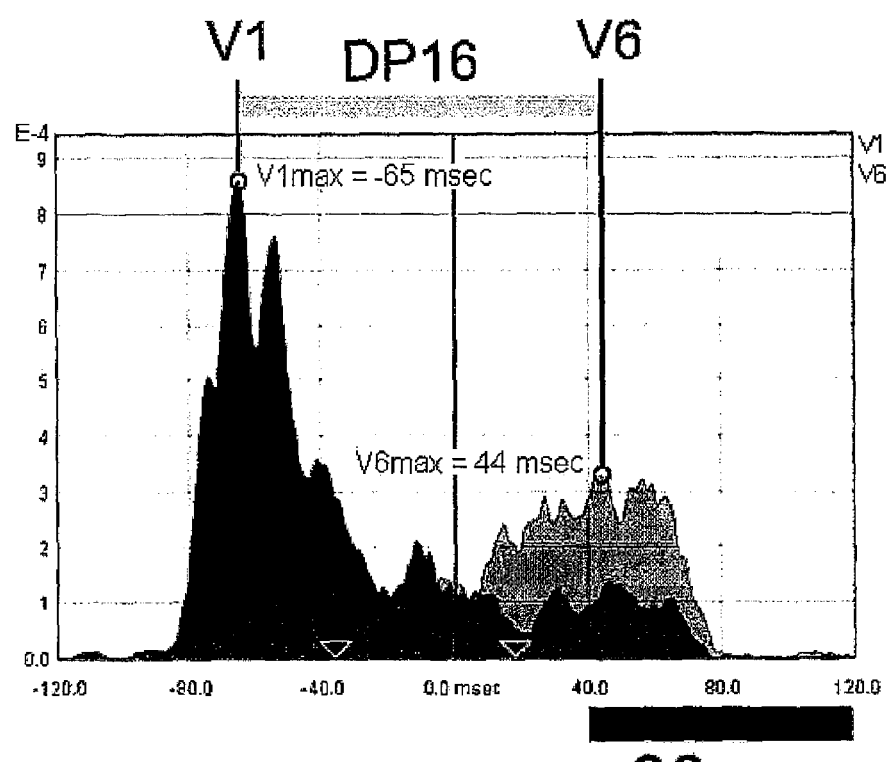
Figure 13B:
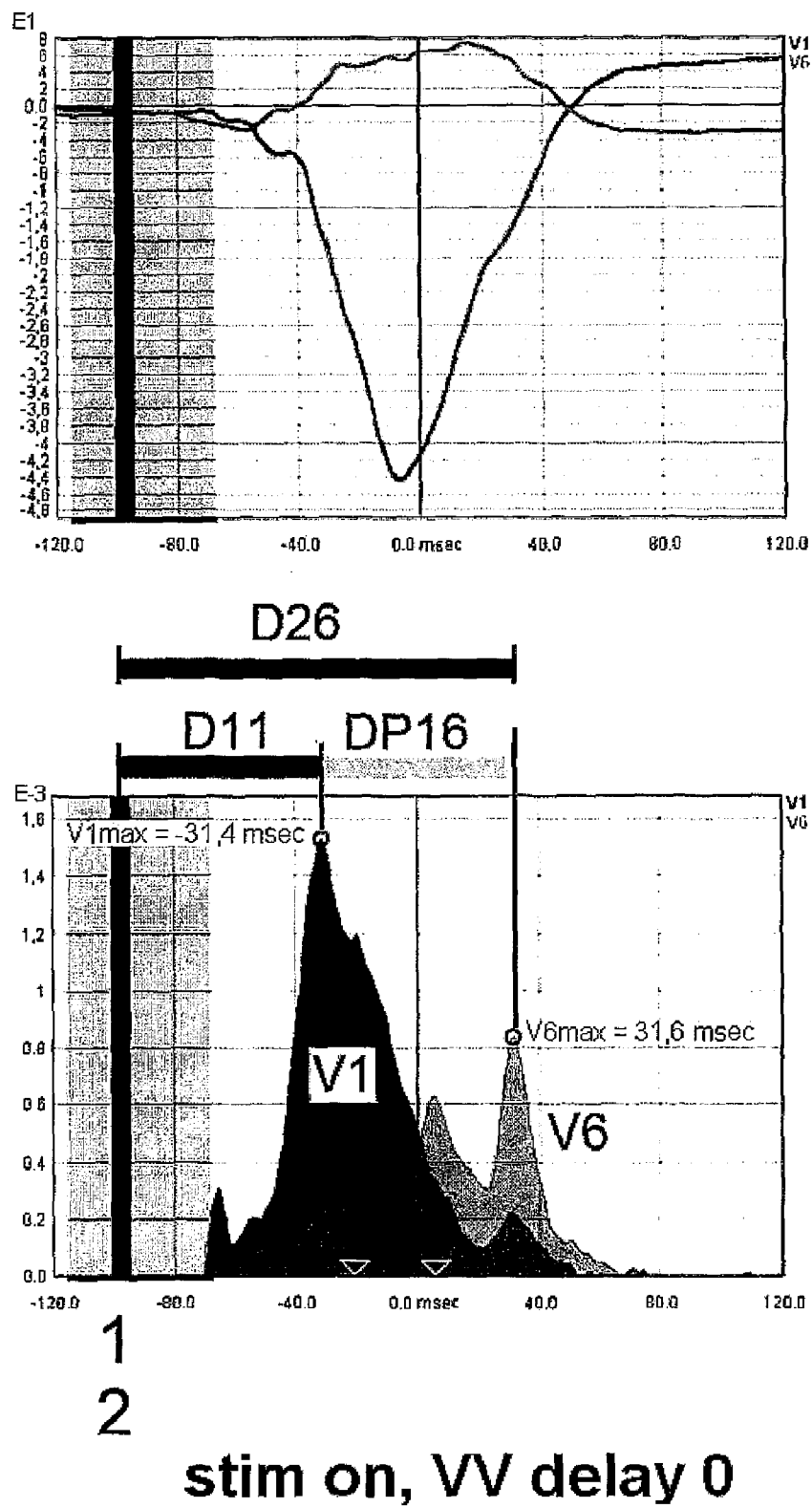
Figure 13C:
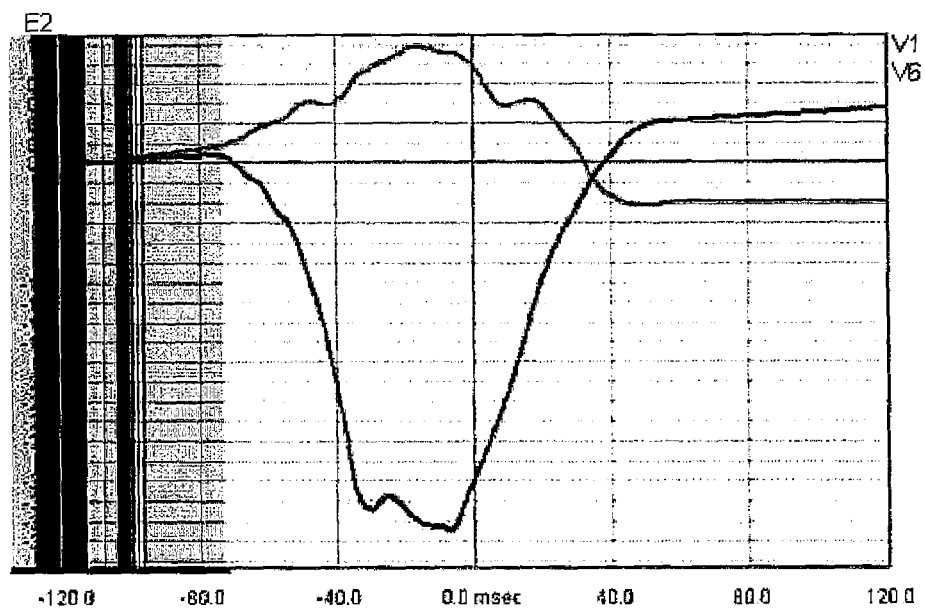
Figure 13C:
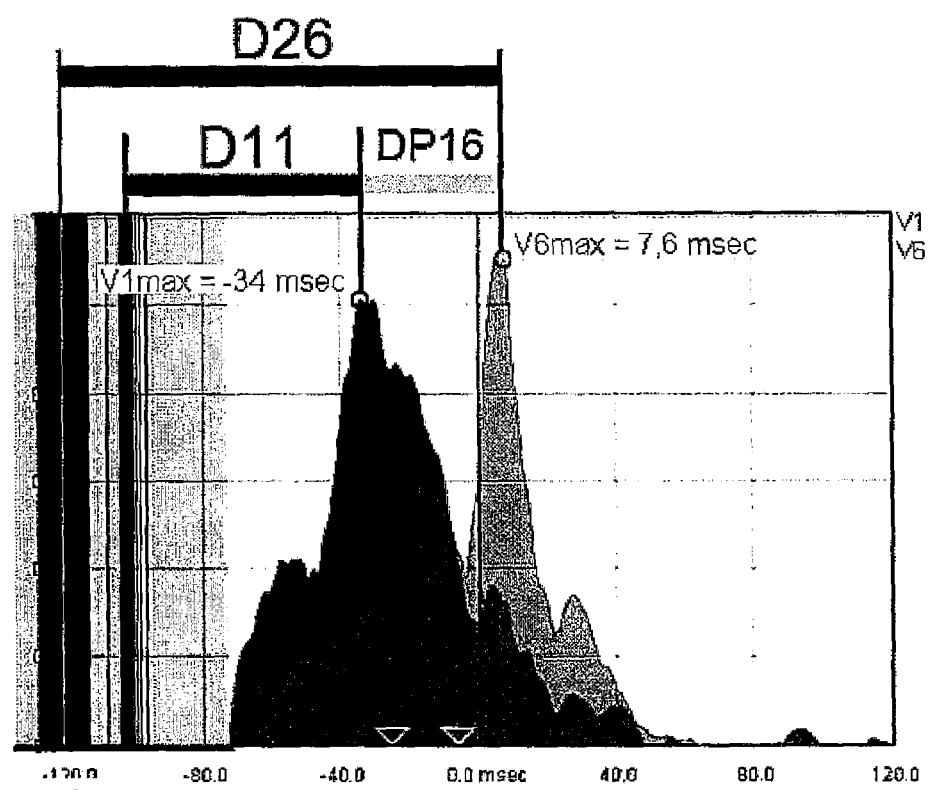

An example of the possibility to determine the electric dyssynchrony of the myocardium by means of the numerical parameters is in FIG. 12. The parameter DPij in milliseconds or in another unit of time is determined from differences of the TNPs for the amplitude or power envelopes position in the individual channels of the EKG signal. The parameter DPij is determined as a difference of the TNPs for the channel i and the channel j. Higher absolute values of the parameters DPij mean a longer time interval between the parameters and thus also the higher electric dyssynchrony of the myocardium. The parameters DPij are further used for a selection of patients suitable for the implementation of the biventricular or multi-chamber stimulator. An example of the patient suitable for the biventricular stimulator implementation is in FIG. 12B. The amplitude envelope maximum from the channel V6 is delayed in relation to the channel V1 maximum by 80 ms. Thus the parameter DP16 is 80 ms. The channel V1 includes first of all electric activation of the right ventricle and the septum, the channel V6 includes electric activation of the lateral wall of the left ventricle. The parameter DP16 can be interpreted as the delay of the electric activation of the left ventricle lateral wall by 80 ms. A patient with this value of the parameter DP16 is suitable for the biventricular stimulator implementation on the ground of proved electric dyssynchrony of the myocardium. An example of a patient with the delayed activation of the right ventricle and a part of the septum is shown in FIG. 12C. The amplitude envelope maximum of the channel V1 marked with dark gray colour is delayed in relation to the amplitude envelope maximum of the channel V6. The channel V1 envelope has two local maximums, the first of which coincides with the maximum of the envelope of the channel V6. It means, that the electric depolarization of the myocardium proceeds at the beginning synchronously with subsequent separate activation of the electric depolarization in the area of the septum and the right ventricle. For patients with already implemented stimulator, the parameters DPij are used to optimise the stimulator setting. The optimization proceeds in such a way that the stimulations in different heart ventricles are time-shifted in relation to each other so that the parameters DPij may be as low as possible. The switched off biventricular stimulator is shown in FIG. 13A. A demonstration of a change of the parameter DP16 after switching on the biventricular stimulator and of a dual setting of the stimulator parameters is depicted in FIGS. 13B and 13C. The synchronous stimulation of the left and the right ventricles is shown in FIG. 13B. In FIG. 13C the stimulation of the left ventricle precedes the stimulation of the right ventricle by 20 ms. In this case the parameter DP16 is lower than in the synchronous stimulation and the setting of the stimulator is more advantageous.

Figure 13D:
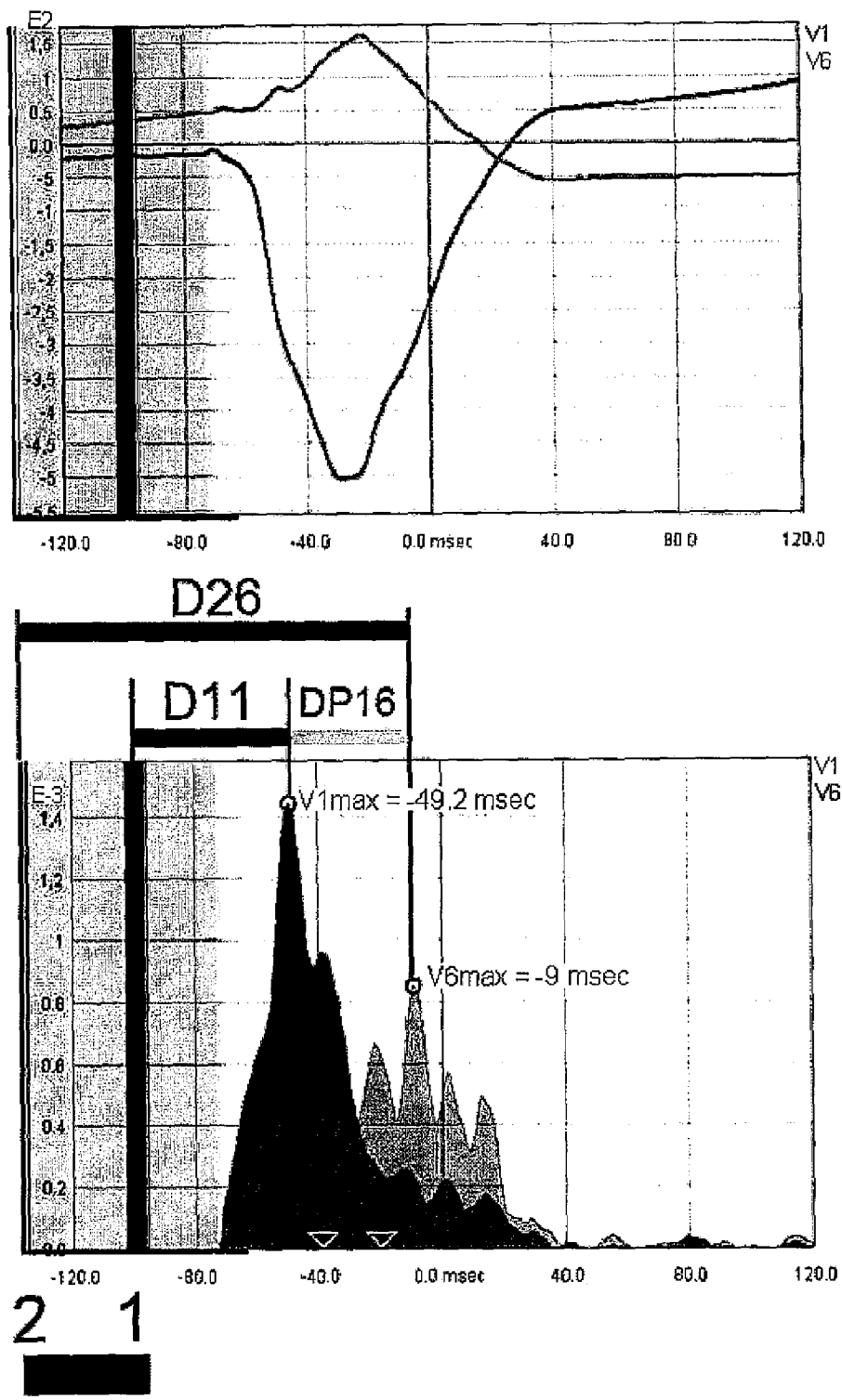
Figure 13E:
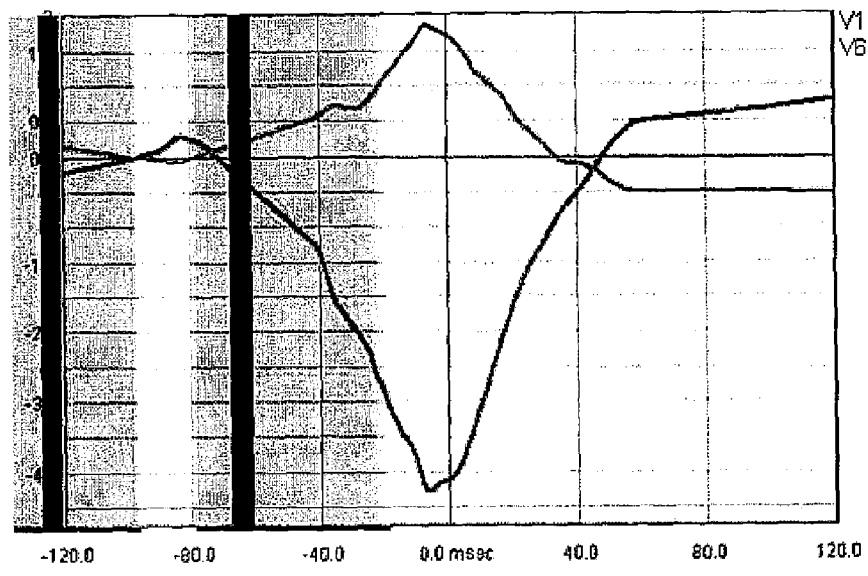
Figure 13E:
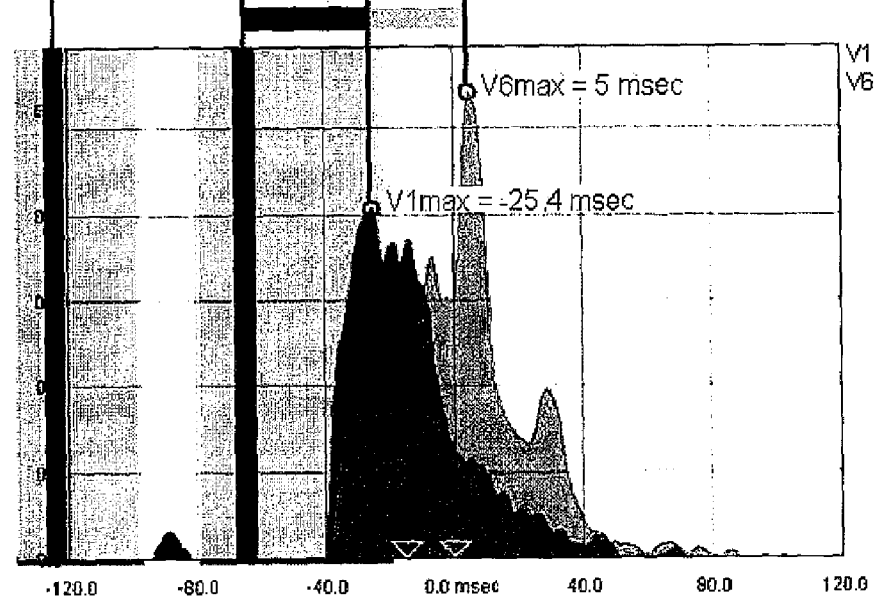

In another advantageous embodiment of the method of the EKG signal processing, with patients with implanted multi-chamber stimulator the stimulating pulses positions on the time axis and their distance from the values of the TNPs for positions of the amplitude or power envelopes in the individual channels of the EKG signal are determined—parameter Dsi in milliseconds or in another unit of time, where sth stimulating pulse and ith EKG channel are defined. Example of various settings of the biventricular stimulator is shown in FIGS. 13B, 13C, 13D and 13E. Number 1 defines the instant of stimulation in the right ventricle, number 2 defines the instant of stimulation in the left ventricle. In FIG. 13B the stimulations in the right and the left ventricles 1 and 2 arise at the same instant of time, in FIG. 13C the stimulation 2 in the left ventricle precedes the stimulation 1 in the right ventricle by 20 ms, in FIG. 13D the stimulation 2 in the left ventricle precedes the stimulation 1 in the right ventricle by 40 ms and in FIG. 13E the stimulation 2 in the left ventricle precedes the stimulation 1 in the right ventricle by 60 ms. The parameters D11 and D26 are depicted in FIGS. 13B, 13C, 13D and 13E. Parameters Dsi indicate a speed of transmission of the stimulating signal into the heart area determinate by the EKG channel. This way it is possible to advantageously evaluate the suitability of the stimulating electrodes position and the characteristics of the electric stimulation propagation in the heart muscle. Lower value of the parameter Dsi signifies faster propagation of the stimulating signal. Higher value of Dsi signifies slower conduction of the stimulating pulse. The slower conduction can be a consequence of an incorrect position of the stimulating electrode or of a slowed-down conduction of the impulse through the heart muscle. When a higher value of preceding the stimulation in the left ventricle in relation to the right ventricle is set, e. g. 60 ms in FIG. 13E, it is possible to evaluate a penetration of the stimulating pulse 2 from the left ventricle to the right ventricle and the septum according to parameters Dsi even before the activation of the right ventricle and the septum by the respective stimulating pulse 1. In such a case the parameter D11 value is lowered, as can be seen in FIGS. 13D and 13E, and thus the time interval between the right ventricle and the septum stimulation and the amplitude envelope maximum in the channel V1, that describes this area best, shortens.

Further according to the invention, the amplitude or power envelopes of the individual channels or the sum of selected channels can be converted to a hearable audio signal in such a way, that the carrier frequency in an audible band within the range of 300 up to 15000 Hz is modulated by the amplitude or power envelope of the individual channels or the sum of the selected channels, whereas these envelopes are spread out in time once up to ten times. The signal is brought to the audio signal generator 11, which enables the EKG analysis by ears.

For a stereophonic reproduction of the ultra high frequency oscillation of EKG the sum of the amplitude or power envelopes of the channels V1, V2 and V3 and the sum of the amplitude or power envelopes of the channels V4, V5 and V6 of the EKG signal are used. These sums are converted to two hearable audio signals with different carrier frequencies for stereophonic reproduction of the ultra high frequency heart activity in the audio signal generator 11. A creation of the signal for the stereophonic reproduction is illustrated in FIGS. 8 and 9.

The measuring and processing of the ultra high frequency EKG oscillation according to this invention provide quite new information on an electric activity of a heart muscle. This information is closely connected with a short depolarizing phase at the beginning of an action potential. The action potential propagates gradually in contractile cells. This process of the propagation is recorded by the apparatus according to this invention. The depolarization initiates a mechanical contraction of the cells. Thus the measuring of the depolarizing phase of the action potentials is closely connected with timing and spatial characteristics of a mechanical activity of the heart.

The apparatus for measuring the ultra high frequency signal of the electrocardiograph and the method of its processing according to this invention enable the early, non-invasive and financially modest diagnostics of serious heart diseases. The analysis of the ultra high frequency components of the EKG signal also enables early identification of different types of pathologies of the ventricle depolarization, e. g. in case of cardiac ischemia, in disorders of heart tissue conductivity, in identification of after-heart attack states and in a stratification of risks of sudden cardiac death or a necessity of ICD implementation. A quantification of the ventricles dyssynchrony is the particularly important sphere of the invention utilization. The current method of this pathological dysfunction description is largely based on a shape and a width of the QRS complex of the EKG signal. This method is commonly considered to be insufficient. Nevertheless, it is the main criterion, because no other sufficiently accurate and available technologies are at the disposal. The distribution of the high frequency oscillation of the EKG signal in the individual leads according to this invention is able to quantify with a great precision the timing of the electric depolarization of the ventricles. The distribution of the amplitude envelopes of a healthy synchronous heart is shown in FIG. 12A, of a heart with a delayed electric activation of the left ventricle in FIG. 12B, and of a heart with a delayed electric activation of the right ventricle caused by a blockade of the right Tawara bundle branch in FIG. 12C. The dark gray colour represents the lead V1, light gray colour represents the lead V6, the gray colour represents overlapping of the envelopes. By means of this invention the delay of the electric activation of one of the ventricles in milliseconds can also be determined. In FIGS. 12B and 12C the delay time is defined by vertical black lines with a time length of 80 ms. This datum is not achievable by any other technology.

The dyssynchrony of the ventricles can be reduced by the biventricular stimulator implantation. At present there are no fully unified and sufficient criteria for the selection of patients suitable for this technology. It is very difficult to determine success rate of the biventricular stimulation as well. Examples of the invention applications in determining patients suitable for the biventricular stimulation and verification of the stimulation effect are shown in FIG. 13. The figure shows the averaged amplitude envelopes within the range of 500-1000 Hz, dark gray colour represents the lead V1, light gray colour represents the lead V6. A candidate with a considerable dyssynchrony of the ventricles 100 ms suitable for the stimulation is in FIG. 13A. The envelopes, when the stimulation has been switched on, are depicted in FIG. 13B. With the stimulation an increase of overlapping the amplitudes from the both leads occurred, and thus the electric synchronization was improved. Another advantageous application of the invention is the possibility to optimize the setting of the biventricular stimulator parameters according to the degree of the overlapping the envelopes or powers from the individual EKG channels.

INDUSTRIAL APPLICABILITY

Applicability in a clinical medicine is exceptionally high first of all because of an easiness of the ultra high frequency EKG signal measuring that differs in no way from the standard measuring of the EKG signal, and because of a high added information value on a time distribution of a depolarization phase of contractile cells of ventricles, which is not available in common EKG record. The parameters obtained by means of this invention provide important information for the determination of the electric inhomogeneity and dyssynchrony of myocardium, selection of patients for the stimulators implementation and optimization of the stimulators setting.

The invention claimed is:

1. A method of processing an EKG signal including a plurality of channels, the method comprising:
   selecting a frequency range above a frequency of 250 Hz on the EKG signal,
   calculating, in the selected frequency range for each channel of the EKG signal, an amplitude envelope or a power envelope of the EKG signal,
   averaging the amplitude envelopes or the power envelopes of each of a first channel and a second channel of the EKG signal over time with respect to a position of $R_m$ of an R wave of the respective envelopes to increase a signal-to-noise ratio of the respective envelopes of each of the first channel and the second channel,
   comparing the averaged amplitude envelopes or the averaged power envelopes of the first and second channels of the EKG signal on a time axis, and
   defining an electric dyssynchrony of ventricles in units of time as a difference between one or more time numerical parameters of the averaged amplitude envelopes or the averaged power envelopes of the first and second channels.

2. The method of processing the EKG signal according to claim 1, further comprising:
   subtracting a median value or a mean value in an interval of a minimum of 100 ms after the position of $R_m$ up to 300 ms after the position of $R_m$ from the averaged amplitude envelopes or power envelopes of the EKG signal to remove a noise background, and
   setting negative values of the respective envelopes to zero after subtracting the median or the mean value.

3. The method of processing the EKG signal according to claim 1, wherein the amplitude envelopes or the power envelopes of the EKG signal are calculated using a Hilbert transformation.

4. The method of processing the EKG signal according to claim 1, wherein the amplitude envelopes are calculated by:
   filtering the EKG signal,
   converting the filtered EKG signal to an absolute value, and
   smoothing the absolute value of the filtered EKG signal.

5. The method of processing the EKG signal according to claim 1, wherein the power envelopes of the EKG signal are calculated by:
   filtering the EKG signal,
   raising the EKG signal to the power of two, and
   smoothing the raised EKG signal.

6. The method of processing the EKG signal according to claim 1, wherein comparing the averaged amplitude envelopes or averaged power envelopes of the channels of the EKG signal on the time axis comprises:
   displaying the amplitude envelopes or the power envelopes of the channels of the EKG signal on a display unit, and
   assigning a color or a degree of shade to each of the channels of the EKG signal displayed.

7. The method of processing the EKG signal according to claim 1, further comprising:
   converting the averaged amplitude envelopes or the averaged power envelopes of each channel of the EKG signal within the range of 300 ms before and 600 ms after the position of $R_m$ of the R wave of a QRS complex to a series of numerical parameters, wherein the numerical parameters include:
      one or more amplitude numerical parameters selected from a group containing a maximum of the averaged amplitude envelopes, a maximum of the averaged power envelopes, an integral of the averaged amplitude envelopes, and an integral of the averaged power envelopes in each of the channels or in sums of the channels and in each frequency range, and
      the one or more time numerical parameters selected from a group containing time positions of the maximums of the averaged amplitude envelopes or the averaged power envelops, time positions of centers of the averaged amplitude envelopes or the averaged power envelops, time positions of beginnings of the averaged amplitude envelopes or the averaged power envelops, and time positions of endings of the averaged amplitude envelopes or the averaged power envelops in each of the channels or in the sums of the channels, and in each of the frequency ranges,
   the time position of the beginning of the averaged amplitude envelopes or the averaged power envelopes in one channel is determined as a first value exceeding the predetermined limit,
   the time position of an end of the averaged amplitude envelopes or the averaged power envelopes in one channel is determined as the last value exceeding the predetermined limit, and
   the predetermined limit is determined as a percentage of the maximum of the averaged amplitude envelopes or the maximum of the averaged power envelopes within a range of 1 to 25 percent.

8. The method of processing the EKG signal according to claim 7, wherein the numerical parameters are normalized by:
   normalizing a first numerical parameter for the selected frequency range, a selected channel, or a selected sum of several channels using a second numerical parameter from another frequency range, another channel, or another sum of the channels,
   wherein the normalized numerical parameter equals the first numerical parameter divided by the second numerical parameter.

9. The method of processing the EKG signal according to claim 7, further comprising:

determining pathological areas of myocardium based on a position the one or more amplitude numerical parameters and the one or more time numerical parameters for the channels, wherein a decrease of the one or more amplitude numerical parameters values and an increase of differences between the one or more time numerical parameters indicate an occurrence of the myocardium pathology in area given by the channels.

10. The method of processing the EKG signal according to claim 9, further comprising:
determining a pathological progression by comparing the one or more amplitude numerical parameters and the one or more time numerical parameters from the channels, recorded over a period of days, weeks, months, and/or years.

11. The method of processing the EKG signal according to claim 1, wherein the difference between the time numerical parameters of the selected channels is further used for selecting patients suitable for a multi-chamber stimulator implementation or for patients with an already implemented stimulator for an optimization of a stimulator function setting by time shifting a stimuli activation in the chambers to reach a minimum absolute value of the difference.

12. The method of processing the EKG signal according to claim 1, further comprising, for patients with a multi-chamber stimulator:
determining, for at least one stimulating pulse on the time axis, a position and a distance of the stimulating pulse from the time numerical parameter in a corresponding channel of the EKG signal in the units of time, and
evaluating, based on the position or the distance of the at least one stimulating pulse from the time numerical parameter, a suitability of positions of one or more stimulating electrodes and characteristics of an electric stimulation in the heart muscle propagation,
wherein a shorter distance corresponds to a higher speed of transmission of the at least one stimulating pulse into the heart area delimitated by the corresponding channel of the EKG signal.

13. The method of processing the EKG signal according to claim 1, further comprising:
converting the amplitude envelopes or the power envelopes of at least one of the channels or a sum of selected channels to a hearable audio signal in such a way that a carrier frequency in a frequency range of 300 to 15000 Hz is modulated by the amplitude envelopes or the power envelopes of the at least one channel or a sum of the selected channels, while the amplitude envelopes or power envelopes are extended in time between one and ten times.

14. The method of processing the EKG signal according to claim 13, wherein the sum of the amplitude envelopes or the power envelopes of a first set of the channels of the EKG signal, or a combination of the amplitude envelopes or the power envelopes of the first set of the channels and the sum of the amplitude envelopes or the power envelopes of a second set of the channels of the EKG signal or a combination of the amplitude envelopes or the power envelopes of the second set of the channels are converted to two hearable audio signals with different carrier frequencies for a stereophonic reproduction of an ultra high frequency heart activity.

15. The method of processing the EKG signal according to claim 1, further comprising:
dividing each channel of the EKG signal into a plurality of consecutive frequency ranges;

arranging the plurality of EKG channels in an EKG map including orthogonal coordinates,
determining the averaged amplitude envelopes or the averaged power envelopes in each frequency range of each channel of the plurality of channels,
displaying the amplitude envelopes or the averaged power envelopes in a three-dimensional matrix including a plurality of elements each corresponding to one of the EKG channels in the EKG map and including a value of a parameter of the respective channel, the amplitude envelopes, or the power envelopes.

16. An apparatus for processing an EKG signal including a plurality of channels, the apparatus comprising:
one or more analogue amplifiers each including an input and an output, the input of each of the analogue amplifiers being connected to an output of a sensor of the EKG signal,
one or more analogue signal to digital signal converters each including an input and an output, the input of each of the analogue signal to digital signal converters being connected to the output of a respective one of the one or more analogue amplifiers,
the sensors, the analogue amplifiers, and the analogue signal to digital signal converters having a dynamic range above 100 dB within their whole transmission band,
a storage unit including one or more inputs and at least one output, the inputs of the storage unit being connected to the outputs of the analogue signal to digital signal converters,
a detector of a position of $R_m$ of an R wave of a QRS complex, the detector including an input and an output, the input of the detector being connected to the output of the storage unit,
a band pass filter including an input and an output, the input of the band pass filter being connected to the output of the detector, and
a calculating unit that includes an input connected to the output of the band pass filter and an output connected to at least one indicating unit, and that is configured to:
select a frequency range above a frequency of 250 Hz on the EKG signal,
calculate, in the selected frequency range for each channel of the EKG signal, amplitude envelopes or power envelopes of the EKG signal,
average the amplitude envelopes or the power envelopes of each of a first channel and a second channel of the EKG signal over time with respect to a position of Rm of an R wave of the respective envelope to increase a signal-to-noise ratio of the respective envelope of each of the first channel and the second channel,
compare the averaged amplitude envelopes or the averaged power envelopes of the first and second channels of the EKG signal on a time axis, and
define an electric dyssynchrony of ventricles in units of time as a difference between one or more time numerical parameters of the averaged amplitude envelopes or the averaged power envelopes of the first and second channels.

17. The apparatus according to claim 16, wherein the indication unit is a display unit for displaying the envelopes or one or more calculated numerical parameters.

18. The apparatus according to claim 16, wherein the indication unit is an audio signal generator.

* * * * *